United States Patent [19]
Pieper et al.

[11] 3,956,492
[45] May 11, 1976

[54] PHARMACEUTICAL COMPOSITIONS CONTAINING A 3-(AMINO-METHYLENE)-5-PHENYL-1,4-BENZODIAZEPIN-2-ONE AND METHOD OF USE

[75] Inventors: Helmut Pieper; Gerd Krüger; Johannes Keck, all of Biberach an der Riss; Klaus-Reinhold Noll, Warthausen-Oberhofen; Joachim Kähling, Biberach an der Riss, all of Germany

[73] Assignee: Boehringer Ingelheim GmbH, Ingelheim am Rhein, Germany

[22] Filed: Dec. 12, 1974

[21] Appl. No.: 532,069

Related U.S. Application Data
[62] Division of Ser. No. 376,378, July 5, 1973, Pat. No. 3,872,090.

[30] Foreign Application Priority Data
July 12, 1972   Germany............................ 2234150
May 15, 1973    Germany............................ 2324962

[52] U.S. Cl.............................. 424/244; 424/246; 424/248; 424/250; 424/267; 424/274
[51] Int. Cl.$^2$.................. A61K 31/33; A61K 31/54; A61K 31/495; A61K 31/535
[58] Field of Search............. 260/239.3 D; 424/244, 424/246, 250, 267, 274, 248

*Primary Examiner*—Stanley J. Friedman
*Attorney, Agent, or Firm*—Hammond & Littell

[57] ABSTRACT
Pharmaceutical dosage unit compositions containing as an active ingredient a compound of the formula

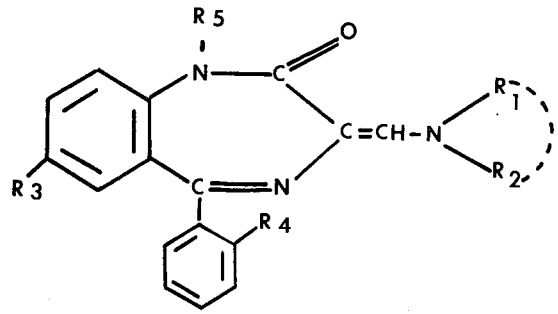

wherein
  $R_1$ and $R_2$, which may be identical to or different from each other, are each hydrogen, cycloalkyl, phenyl, —A—Y
wherein
  A is alkyl of 1 to 5 carbon atoms or alkenyl of 1 to 5 carbon atoms, and
  Y is furyl, dialkylamino, hydroxyl, carbalkoxy or carbamido,
or, together with each other and the nitrogen atom to which they are attached, pyrrolidino, piperidino, hexamethyleneimino, morpholino, thiomorpholino, thiomorpholino-S-oxide or N'-alkylpiperazino,
  $R_3$ is halogen, nitro or trifluoromethyl,
  $R_4$ is hydrogen, halogen or trifluoromethyl, and
  $R_5$ is hydrogen, alkyl, cycloalkyl-methyl, alkylamino-alkyl, dialkylamino-alkyl or trifluoromethyl-alkyl;
and a method of using the same as sedatives, tranquilizers, muscle-relaxants and anticonvulsives.

20 Claims, No Drawings

PHARMACEUTICAL COMPOSITIONS CONTAINING A 3-(AMINO-METHYLENE)-5-PHENYL-1,4-BENZODIAZEPIN-2-ONE AND METHOD OF USE

This is a division of copending application Ser. No. 376,378, filed July 5, 1973, now U.S. Pat. No. 3,872,090.

This invention relates to novel pharmaceutical compositions containing a 3-(amino-methylene)-5-phenyl-1,4-benzodiazepin-2-one, as well as to a method of using the same as sedatives, tranquilizers, muscle-relaxants and anti-convulsives.

More particularly, the present invention relates to novel pharmaceutical compositions containing as an active ingredient a compound of the formula

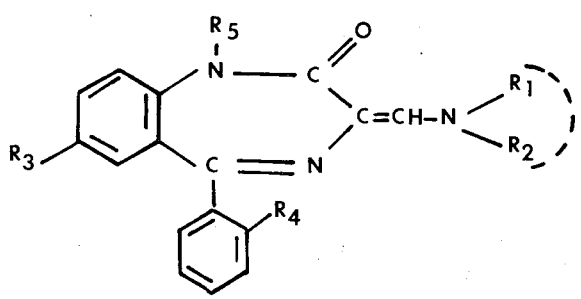

(I)

wherein $R_1$ and $R_2$, which may be identical to or different from each other, are each hydrogen, cycloalkyl, phenyl, —A—Y where A is alkyl of 1 to 5 carbon atoms or alkenyl of 1 to 5 carbon atoms, and Y is furyl, dialkylamino, hydroxyl, carbalkoxy or carbamido, or, together with each other and the nitrogen atom to which they are attached, pyrrolidino, piperidino, hexamethyleneimino, morpholino, thiomorpholino, thiomorpholino-S-oxide or N'-lower alkyl-piperazino, $R_3$ is halogen, nitro or trifluoromethyl, $R_4$ is hydrogen, halogen or trifluoromethyl, and $R_5$ is hydrogen, lower alkyl, cycloalkyl-methyl, lower alkylamino-lower alkyl, di-lower alkylamino-lower alkyl or trifluoro-methyl-lower alkyl.

The compounds embraced by formula I may be prepared by the following methods, inter alia:

Method A

For the preparation of a compound of the formula I wherein A, $R_3$, $R_4$ and $R_5$ have the same meanings as in formula I, $R_1$ and $R_2$ have the same meanings as in formula I except thiomorpholino-S-oxide, or hydrogen, and Y has the same meanings as in formula I except hydroxyl, carbalkoxy and carbamido, by reacting a 5-phenyl-1,4-benzodiazepin-2-one of the formula

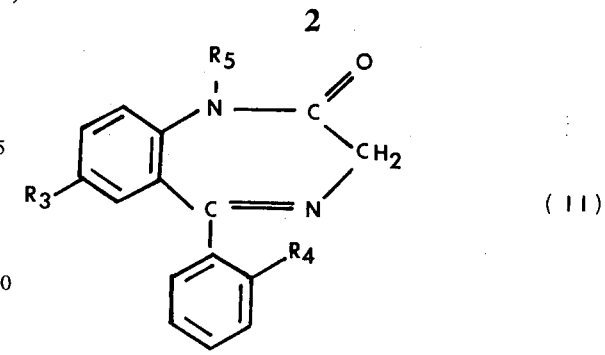

(II)

wherein $R_3$, $R_4$ and $R_5$ have the meanings previously defined, with a formamide-acetal of the formula

(III)

wherein $R_1'$ and $R_2'$, which may be identical to or different from each other, are each cycloalkyl, phenyl, —A—Y' where

A has the same meanings as in formula I, and

Y' is furyl or di(lower alkyl)amino, or, together with each other and the nitrogen atom to which they are attached, pyrrolidino, piperidino, hexamethyleneimino, morpholino, thio-morpholino or N'-lower alkyl-piperazino, and $R_6$ is lower alkyl.

The reaction is advantageously carried out under exclusion of moisture and in a solvent medium at a temperature between 20° and 160°C., preferably between 100° and 140°C. Examples of suitable solvent media are inert solvents, such as tetrahydrofuran, dioxane or dimethylformamide, or preferably, however, a sufficient excess of the formamide-acetal of the formula III over and above the stoichiometrically required amount. The reaction will also proceed in the absence of a solvent medium.

Method B

By reacting a compound of the formula

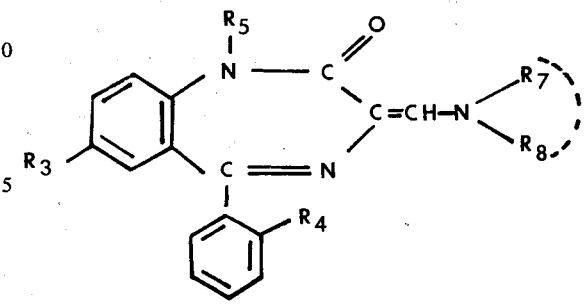

(IV)

wherein $R_3$, $R_4$ and $R_5$ have the same meanings as in formula I, and $R_7$ and $R_8$, which may be identical to or different from each other, are each optionally substituted alkyl, optionally substituted aryl or, together with each other and the nitrogen atom to which they are attached, form a heterocyclic ring, but preferably alkyl of 1 to 3 carbon atoms, with an amine of the formula

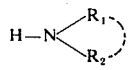 (V)

wherein $R_1$ and $R_2$ have the same meanings as in formula I.

The reaction is advantageously performed under exclusion of moisture in a solvent medium, and optionally in the presence of a catalytic amount of an acid addition salt, such as the hydrochloride, of the amine of the formula V, at a temperature between 50° and 160°C, preferably between 80° and 140°C. Examples of suitable solvent media are inert organic solvents, such as tetrahydrofuran, dioxane or dimethylformamide, or a sufficient excess of the amine of the formula V over and above the stoichiometrically required amount. The reaction may, however, also be performed without a solvent medium.

Method C

In those instances where method A or B yields as an end product a compound of the formula I wherein $R_5$ is hydrogen and $R_1$ and $R_2$ do not contain a reactive hydrogen atom, such a compound can be alkylated in the 1-position by reacting it with a substituted alkyl halide of the formula Hal - $R_5'$ (VI)

wherein $R_5'$ has the same meanings as $R_5$ in formula I except hydrogen, and

Hal is chlorine, bromine or iodine, preferably in the presence of a strong base, such as sodium hydride or sodium methylate, in an inert solvent such as dimethylformamide, and advantageously at room temperature.

A starting compound of the formula II may be obtained by known methods, such as by reacting a correspondingly substituted 2-amino-benzophenone with a haloacetic acid halide, followed by cyclization of the intermediate with ammonia. If a compound of the formula II wherein $R_5$ is hydrogen is obtained in this manner, the same may be converted into the corresponding compound wherein $R_5$ has the other meanings defined above by reaction with an alkyl halide of the formula VI [see Chem. Reviews 86, 747–785 (1968): and J. Pharm. Sci. 53, 577–590 (1969)].

A starting compound of the formula IV may be obtained by reacting a corresponding 1,3-dihydro-1,4-benzodiazepin-2-one with a corresponding formamide-acetal in analogy to method A.

The following example further illustrate the present invention and will enable others skilled in the art to understand it more completely. It should be understood, however, that the invention is not limited solely to the particular examples given below.

EXAMPLE 1

7-Chloro-5-(2'-chloro-phenyl)-1,3-dihydro-3-(dimethylaminomethylene)-1-methyl-2H-1,4-benzodiazepin-2-one by method A A suspension of 55 gm of 7-chloro-5-(2'-chlorophenyl)-1,3-dihydro-1-methyl-2H-1,4-benzodiazepin-2-one in 85 ml of N,N-dimethyl-formamide diethylacetal was heated to 130°C in a vessel equipped with a descending condenser, whereby a clear solution was formed after a short time. The temperature of the reaction solution was maintained at 130°C for 41 hours, during which time the ethanol formed by the reaction slowly distilled over. Thereafter, the reaction solution was cooled to about 80°C and then admixed with 50 ml of isopropanol. Upon further cooling of the mixture, a reddish-orange crystalline substance separated out which was collected by vacuum filtration, washed with petroleum ether and recrystallized from isopropanol, whereupon it had a melting point of 202°–203°C. It was identified to be the compound of the formula

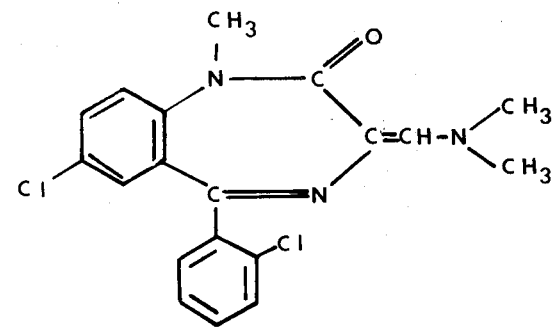

EXAMPLE 2

7-Chloro-5-(2'-chloro-phenyl)-1,3-dihydro-3-(dimethylaminomethylene)-2H-1,4-benzodiazepin-2-one by method A A suspension of 50 gm of 7-chloro-5-(2'-chlorophenyl)-1,3-dihydro-2H-1,4-benzodiazepin-2-one in 100 ml of N,N-dimethyl-formamide diethylacetal was heated to 130°C in a vessel equipped with a descending condenser, whereby a clear solution was formed after a short time. The temperature of the reaction solution was maintained at 130°C for 40 minutes, during which time the ethanol formed by the reaction slowly distilled over. Thereafter, the reaction solution was allowed to cool, and the red precipitate was collected by vacuum filtration, washed with petroleum ether and recrystallized from methanol, whereupon it had a melting point of 239°–241°C. It was identified to be the compound of the formula

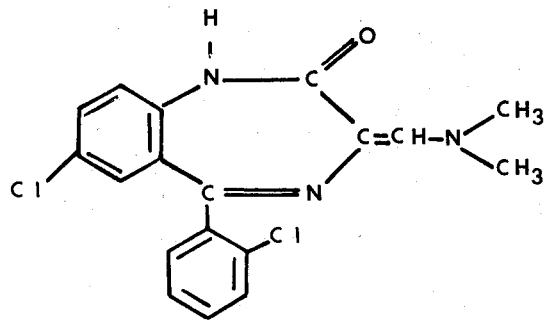

EXAMPLE 3

3-(Ethylamino-methylene)-7-chloro-5-(2'-chloro-phenyl)-1,3-dihydro-2H-1,4-benzodiazepin-2-one by method B A mixture consisting of 5 gm of 7-chloro-5-(2'-chloro-phenyl)-1,3-dihydro-3-(dimethylamino-methylene)-2H-1,4-benzodiazepin-2-one and 75 ml of ethylamine was heated for 20 minutes at 100°C in closed tube. Thereafter, the reaction mixture was quickly cooled, diluted with chloroform and evaporated to dryness in vacuo. The yellow, solid residue was recrystallized from absolute ethanol, yielding the compound of the formula

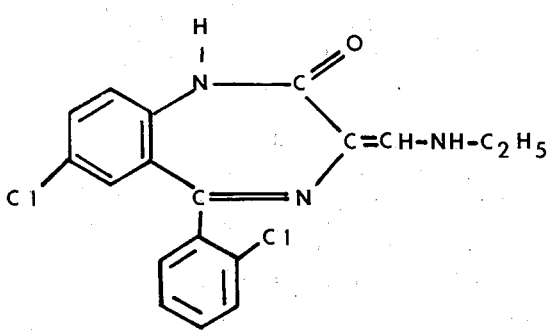

which had a melting point of 213°–215°C.

EXAMPLE 4

7-Chloro-5-(2'-chloro-phenyl)-1,3-dihydro-3-(dimethylaminomethylene)-1-methyl-2H-1,4-benzodiazepin-2-one by method C 35.6 gm of a methanolic 30% sodium methylate solution were added dropwise to a solution of 46.5 gm of 7-chloro-5-(2'-chloro-phenyl)-1,3-dihydro-3-(dimethylamino-methylene)-2H-1,4-benzodiazepin-2-one in 300 ml of dry dimethylformamide at room temperature, accompanied by stirring, and the resulting mixture was stirred for 30 minutes more at room temperature and subsequently cooled to +5°C while stirring. Then, while maintaining that temperature by cooling, 58 gm of methyl iodide were added at a slow dropwise rate, again while stirring, and the resulting mixture was stirred for 90 minutes more at +5°C. Thereafter, the yellow precipitate which had formed was collected by vacuum filtration, washed with much water, dried and recrystallized from isopropanol, yielding the compound named in the heading above, which had a melting point of 199°–200°C.

EXAMPLE 5

7-Bromo-5-(2'-chloro-phenyl)-1,3-dihydro-1-methyl-3-[N-methyl-N-(morpholinocarbonyl-methyl)-amino-methylene]-2H-1,4-benzodiazepin-2-one by method A A suspension of 8.4 gm of 7-bromo-5-(2'-chloro-phenyl)-1,3-dihydro-3-(dimethylamino-methylene)-1-methyl-2H-1,4-benzodiazepin-2-one in 45 gm of sarcosine morpholide was heated to 160°C, while stirring, whereby a clear solution was formed after some time, which was stirred for 90 minutes more at 160°C. Thereafter, the reaction mixture was allowed to cool and was then taken up in a mixture consisting of 150 ml each of tetrahydrofuran and ether. The resulting solution was washed three times with 100 ml of water each, and the organic phase was dried over magnesium sulfate and evaporated in vacuo. The residue was purified on a silicagel column, using a 19:1-mixture of chloroform and methanol as the flow agent. Those fractions containing the desired compound were combined, the solvent mixture was distilled off in vacuo, and the residue was recrystallized from tetrahydrofuran, yielding the compound of the formula

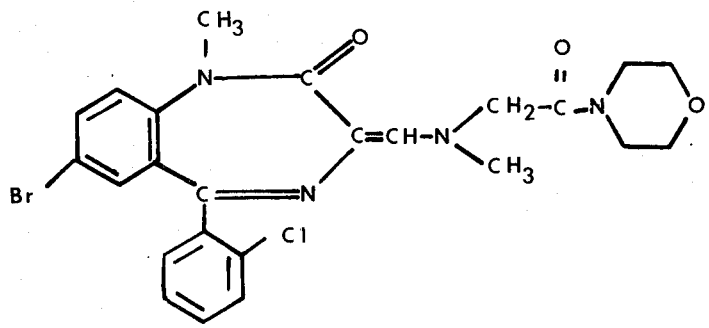

which had a melting point of 200°–202°C.

EXAMPLE 6

Using a procedure analogous to that described in Example 2, 3-(dimethylamino-methylene)-5-phenyl-7-chloro-1,3-dihydro-2H-1,4-benzodiazepin-2-one, m.p. 237°–240°C, of the formula

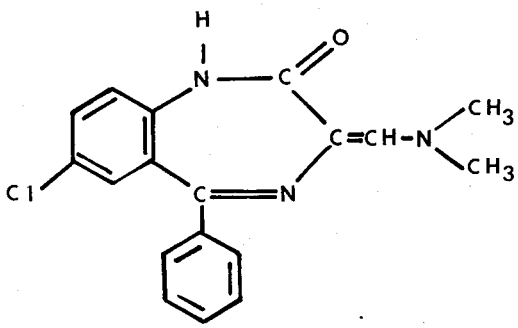

was prepared from 5-phenyl-7-chloro-1,3-dihydro-2H-1,4-benzodiazepin-2-one and N,N-dimethyl-formamide-diethylacetal.

EXAMPLE 7

Using a procedure analogous to that described in Example 1, 1-methyl-3-(dimethylamino-methylene)-5-phenyl-7-chloro-1,3-dihydro-2H-1,4-benzodiazepin-2-one, m.p. 204°–205°C, was prepared from 1-methyl-5-phenyl-7-chloro-1,3-dihydro-2H-1,4-benzodiazepin-2-one and N,N-dimethylformamide-diethylacetal.

EXAMPLE 8

Using a procedure analogous to that described in Example 1, 1-methyl-3-[(N-ethyl-N-methyl-amino)-methylene]-5-phenyl-7-chloro-1,3-dihydro-2H-1,4-benzodiazepin-2-one, m.p. 98°–110°C, was prepared from 1-methyl-5-phenyl-7-chloro-1,3-dihydro-2H-1,4-benzodiazepin-2-one and (N-ethyl-N-methyl-formamide)-diethylacetal.

EXAMPLE 9

Using a procedure analogous to that described in Example 2, 3-(diethylamino-methylene)-5-phenyl-7-chloro-1,3-dihydro-2H-1,4-benzodiazepin-2-one, m.p. 236°–238°C, was prepared from 5-phenyl-7-chloro-1,3-dihydro-2H-1,4-benzodiazepin-2-one and N,N-diethyl-formamide-diethylacetal.

EXAMPLE 10

Using a procedure analogous to that described in Example 1, 1-methyl-3-(diethylamino-methylene)-5-phenyl-7-chloro-1,3-dihydro-2H-1,4-benzodiazepin-2-one, m.p. 192°–194°C, was prepared from 1-methyl-5-phenyl-7-chloro-1,3-dihydro-2H-1,4-benzodiazepin-2-one and N,N-diethyl-formamide-diethylacetal.

EXAMPLE 11

Using a procedure analogous to that described in Example 2, 3-(di-n-propylamino-methylene)-5-phenyl-7-chloro-1,3-dihydro-2H-1,4-benzodiazepin-2-one, m.p. 200°–201°C, was prepared from 5-phenyl-7-chloro-1,3-dihydro-2H-1,4-benzodiazepin-2-one and N,N-di-n-propyl-formamide-diethylacetal.

EXAMPLE 12

Using a procedure analogous to that described in Example 1, 1-methyl-3-(di-n-propylamino-methylene)-5-phenyl-7-chloro-1,3-dihydro-2H-1,4-benzodiazepin-2-one, m.p. 134°–135°C, was prepared from 1-methyl-5-phenyl-7-chloro-1,3-dihydro-2H-1,4-benzodiazepin-2-one and N,N-di-n-propyl-formamide-diethylacetal.

EXAMPLE 13

Using a procedure analogous to that described in Example 2, 3-(diallylamino-methylene)-5-phenyl-7-chloro-1,3-dihydro-2H-1,4-benzodiazepin-2-one, m.p. 173°–175°C, of the formula

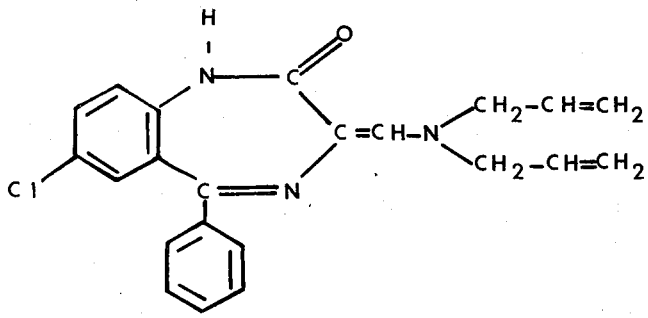

was prepared from 5-phenyl-7-chloro-1,3-dihydro-2H-1,4-benzodiazepin-2-one and N,N-diallyl-formamide-diethylacetal.

EXAMPLE 14

Using a procedure analogous to that described in Example 2, 3-(di-n-butylamino-methylene)-5-phenyl-7-chloro-1,3-dihydro-2H-1,4-benzodiazepin-2-one, m.p. 138°–140°C, was prepared from 5-phenyl-7-chloro-1,3-dihydro-2H-1,4-benzodiazepin-2-one and N,N-di-n-butyl-formamide-diethylacetal.

EXAMPLE 15

Using a procedure analogous to that described in Example 1, 1-methyl-3-(di-n-butylamino-methylene)-5-phenyl-7-chloro-1,3-dihydro-2H-1,4-benzodiazepin-2-one, m.p. 95°–97°C, was prepared from 1-methyl-5-phenyl-7-chloro-1,3-dihydro-2H-1,4-benzodiazepin-2-one and N,N-di-n-butyl-formamide-diethylacetal.

EXAMPLE 16

Using a procedure analogous to that described in Example 2, 3-(diisopropylamino-methylene)-5-phenyl-7-chloro-1,3-dihydro-2H-1,4-benzodiazepin-2-one, m.p. 248°–250°C, was prepared from 5-phenyl-7-chloro-1,3-dihydro-2H-1,4-benzodiazepin-2-one and N,N-diisopropyl-formamide-diethylacetal.

EXAMPLE 17

Using a procedure analogous to that described in Example 1, 1-methyl-3-(diisopropylamino-methylene)-5-phenyl-7-chloro-1,3-dihydro-2H-1,4-benzodiazepin-2-one, an amorphous foam (proof of structure by IR-, UV- and NMR-spectra), was prepared from 1-methyl-5-phenyl-7-chloro-1,3-dihydro-2H-1,4-benzodiazepin-2-one and N,N-diisopropyl-formamide-diethylacetal.

EXAMPLE 18

Using a procedure analogous to that described in Example 2, 3-[(N-cyclohexyl-N-methyl-amino)-methylene]-5-phenyl-7-chloro-1,3-dihydro-2H-1,4-benzodiazepin-2-one, m.p. 247°–250°C, of the formula

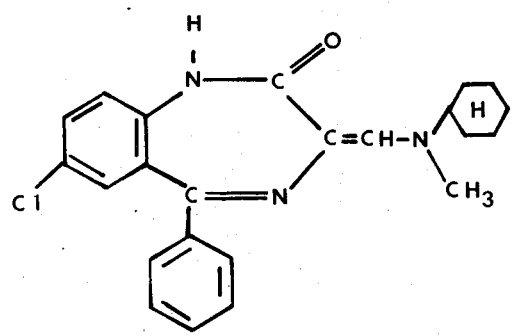

was prepared from 5-phenyl-7-chloro-1,3-dihydro-2H-1,4-benzodiazepin-2-one and (N-cyclohexyl-N-methyl-formamide)-diethylacetal.

EXAMPLE 19

Using a procedure analogous to that described in Example 1, 1-methyl-3-[(N-cyclohexyl-N-methyl-amino)-methylene]-5-phenyl-7-chloro-1,3-dihydro-2H-1,4-benzodiazepin-2-one, m.p. 167°–169°C, was prepared from 1-methyl-5-phenyl-7-chloro-1,3-dihydro-2H-1,4-benzodiazepin-2-one and (N-cyclohexyl-N-methyl-formamide)-diethylacetal.

EXAMPLE 20

Using a procedure analogous to that described in Example 2, 3-(pyrrolidino-methylene)-5-phenyl-7-chloro-1,3-dihydro-2H-1,4-benzodiazepin-2-one, m.p. 252°–254°C, of the formula

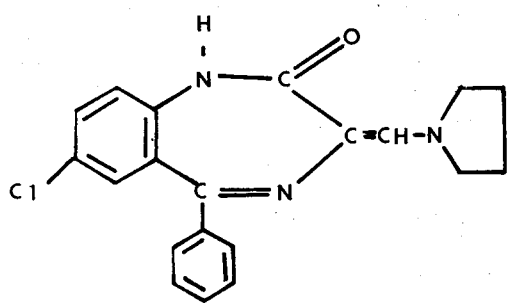

was prepared from 5-phenyl-7-chloro-1,3-dihydro-2H-1,4-benzodiazepin-2-one and pyrrolidino-diethoxy-methane.

EXAMPLE 21

Using a procedure analogous to that described in Example 1, 1-methyl-3-(pyrrolidino-methylene)-5-phenyl-7-chloro-1,3-dihydro-2H-1,4-benzodiazepin-2-one, m.p. 184°–186°C, was prepared from 1-methyl-5-phenyl-7-chloro-1,3-dihydro-2H-1,4-benzodiazepin-2-one and pyrrolidino-diethoxy-methane.

EXAMPLE 22

Using a procedure analogous to that described in Example 2, 3-(piperidino-methylene)-5-phenyl-7-chloro-1,3-dihydro-2H-1,4-benzodiazepin-2-one, m.p. 242°–243°C, of the formula

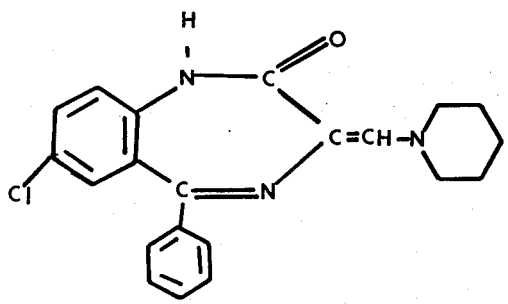

was prepared from 1-methyl-5-phenyl-7-chloro-1,3-dihydro-2H-1,4-benzodiazepin-2-one and piperidino-diethoxy-methane.

EXAMPLE 23

Using a procedure analogous to that described in Example 1, 1-methyl-3-(piperidino-methylene)-5-phenyl-1,3-dihydro-2H-1,4-benzodiazepin-2-one, m.p. 158°C (decomp.), was prepared from 1-methyl-5-phenyl-7-chloro-1,3-dihydro-2H-1,4-benzodiazepin-2-one and piperidino-diethoxy-methane.

EXAMPLE 24

Using a procedure analogous to that described in Example 2, 3-(hexamethyleneimino-methylene)-5-phenyl-7-chloro-1,3-dihydro-2H-1,4-benzodiazepin-2-one, m.p. 248°–250°C, of the formula

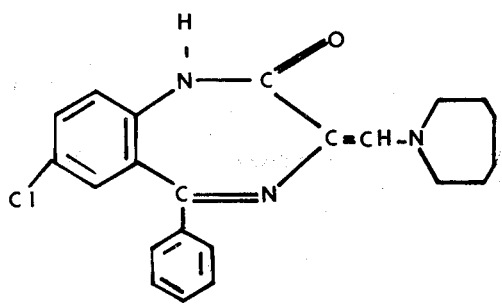

was prepared from 5-phenyl-7-chloro-1,3-dihydro-2H-1,4-benzodiazepin-2-one and hexamethyleneimino-diethoxy-methane.

EXAMPLE 25

Using a procedure analogous to that described in Example 1, 1-methyl-3-(hexamethylenedimino-methylene)-5-phenyl-7-chloro-1,3-dihydro-2H-1,4-benzodiazepin-2-one, m.p. 196°–198°C, was prepared from 1-methyl-5-phenyl-7-chloro-1,3-dihydro-2H-1,4-benzodiazepin-2-one and hexamethyleneimino-diethoxy-methane.

EXAMPLE 26

Using a procedure analogous to that described in Example 2, 3-(morpholino-methylene)-5-phenyl-7-chloro-1,3-dihydro-2H-1,4-benzodiazepin-2-one, m.p. 251°–252°C (decomp.), of the formula

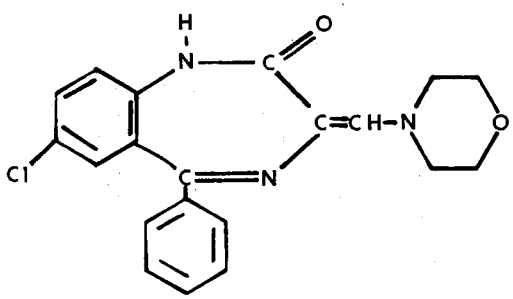

was prepared from 5-phenyl-7-chloro-1,3-dihydro-2H-1,4-benzodiazepin-2-one and morpholino-diethoxy-methane.

EXAMPLE 27

Using a procedure analogous to that described in Example 1, 1-methyl-3-(morpholino-methylene)-5-phenyl-7-chloro-1,3-dihydro-2H-1,4-benzodiazepin-2-one, m.p. 169°–171°C, was prepared from 1-methyl-5-phenyl-7-chloro-1,3-dihydro-2H-1,4-benzodiazepin-2-one and morpholino-diethoxy-methane.

EXAMPLE 28

Using a procedure analogous to that described in Example 1, 1-methyl-3-[(N'-methyl-piperazino)-methylene]-5-phenyl-7-chloro-1,3-dihydro-2H-1,4-benzodiazepin-2-one, m.p. 141°–143°C, for the formula

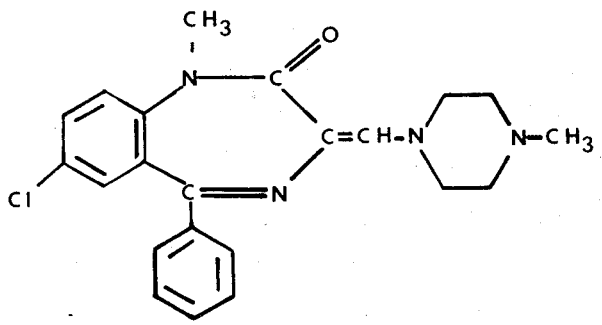

was prepared from 1-methyl-5-phenyl-7-chloro-1,3-dihydro-2H-1,4-benzodiazepin-2-one and (N'-methyl-piperazino)-diethoxy-methane.

EXAMPLE 29

Using a procedure analogous to that described in Example 1, 1-methyl-3-[(N-methyl-N-ethylamino)-methylene]-5-(2'-chloro-phenyl)-7-chloro-1,3-dihydro-2H-1,4-benzodiazepin-2-one, m.p. 88°–91°C, was prepared from 1-methyl-5-(2'-chloro-phenyl)-7-chloro-1,3-dihydro-2H-1,4-benzodiazepin-2-one and (N-methyl-N-ethyl-formamide)-diethylacetal.

EXAMPLE 30

Using a procedure analogous to that described in Example 2, 3-(diethylamino-methylene)-5-(2'-chloro-phenyl)-7-chloro-1,3-dihydro-2H-1,4-benzodiazepin-2-one, m.p. 204°–206°C, was prepared from 5-(2'-chloro-phenyl)-7-chloro-1,3-dihydro-2H-1,4-benzodiazepin-2-one and N,N-diethyl-formamide-diethylacetal.

EXAMPLE 31

Using a procedure analogous to that described in Example 2, 3-(di-n-propylamino-methylene)-5-(2'-chloro-phenyl)-7-chloro-1,3-dihydro-2H-1,4-benzodiazepin-2-one, m.p. 226°–227°C, was prepared from 5-(2'-chloro-phenyl)-7-chloro-1,3-dihydro-2H-1,4-benzodiazepin-2-one and N,N-di-n-propylformamide-diethylacetal.

EXAMPLE 32

Using a procedure analogous to that described in Example 2, 3-(diallylamino-methylene)-5-(2'-chloro-phenyl)-7-chloro-1,3-dihydro-2H-1,4-benzodiazepin-2-one, m.p. 165°–167°C, was prepared from 5-(2'-chloro-phenyl)-7-chloro-1,3-dihydro-2H-1,4-benzodiazepin-2-one and N,N-diallyl-formamide-diethylacetal.

EXAMPLE 33

Using a procedure analogous to that described in Example 2, 3-(di-n-butylamino-methylene)-5-(2'-chloro-phenyl)-7-chloro-1,3-dihydro-2H-1,4-benzodiazepin-2-one, m.p. 211°–213°C, was prepared from 5-(2'-chloro-phenyl)-7-chloro-1,3-dihydro-2H-1,4-benzodiazepin-2-one and N,N-di-n-butyl-formamide-diethylacetal.

EXAMPLE 34

Using a procedure analogous to that described in Example 2, 3-(diisopropylamino-methylene)-5-(2'-chloro-phenyl)-7-chloro-1,3-dihydro-2H-1,4-benzodiazepin-2-one, m.p. 222°–224°C, was prepared from 5-(2'-chloro-phenyl)-7-chloro-1,3-dihydro-2H-1,4-benzodiazepin-2-one and N,N-diisopropylformamide-diethylacetal.

EXAMPLE 35

Using a procedure analogous to that described in Example 2, 3-[(N-β-dimethylamino-ethyl-N-methylamino)-methylene]-5-(2'-chloro-phenyl)-7-chloro-1,3-dihydro-2H-1,4-benzodiazepin-2-one, m.p. 202°–205°C, of the formula

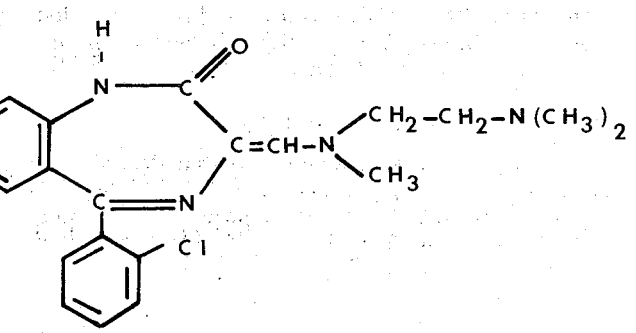

was prepared from 5-(2'-chloro-phenyl)-7-chloro-1,3-dihydro-2H-1,4-benzodiazepin-2-one and [N-(β-dimethylamino-ethyl)-N-methyl-formamide]-diethylacetal.

EXAMPLE 36

Using a procedure analogous to that described in Example 1, 1-methyl-3-[(N-β-dimethylamino-ethyl-N-methylamino)-methylene]-5-(2'-chloro-phenyl)-7-chloro-1,3-dihydro-2H-1,4-benzodiazepin-2-one, m.p. 130°–132°C, was prepared from 1-methyl-5-(2'-chloro-phenyl)-7-chloro-1,3-dihydro-2H-1,4-benzodiazepin-2-one and [N-(β-dimethylamino-ethyl)-N-methyl-formamide]-diethylacetal.

EXAMPLE 37

Using a procedure analogous to that described in Example 1, 1-methyl-3-[(N-methyl-anilino)-methylene]-5-(2'-chloro-phenyl)-7-chloro-1,3-dihydro-2H-1,4-benzodiazepin-2-one, m.p. 197°–199°C, of the formula

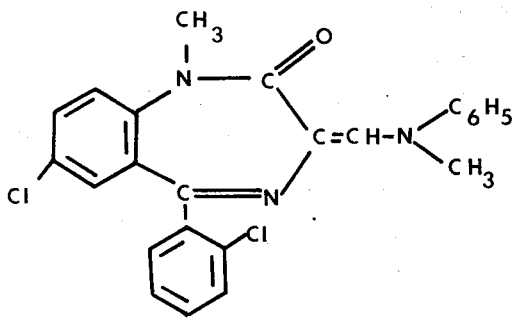

was prepared from 1-methyl-5-(2'-chloro-phenyl)-7-chloro-1,3-dihydro-2H-1,4-benzodiazepin-2-one and (N-methyl-anilino)-diethoxy-methane.

EXAMPLE 38

Using a procedure analogous to that described in Example 2, 3-[(N-cyclohexyl-N-methyl-amino)-methylene]-5-(2'-chloro-phenyl)-7-chloro-1,3-dihydro-2H-1,4-benzodiazepin-2-one, m.p. 197°–200°C, was prepared from 5-(2'-chloro-phenyl)-7-chloro-1,3-dihydro-2H-1,4-benzodiazepin-2-one and (N-cyclohexyl-N-methyl-formamide)-diethylacetal.

EXAMPLE 39

Using a procedure analogous to that described in Example 2, 3-(pyrrolidino-methylene)-5-(2'-chloro-phenyl)-7-chloro-1,3-dihydro-2H-1,4-benzodiazepin-2-one, m.p. 247°–249°C, was prepared from 5-(2'-chloro-phenyl)-7-chloro-1,3-dihydro-2H-1,4-benzodiazepin-2-one and pyrrolidino-diethoxy-methane.

EXAMPLE 40

Using a procedure analogous to that described in Example 2, 3-(piperidino-methylene)-5-(2'-chloro-phenyl)-7-chloro-1,3-dihydro-2H-1,4-benzodiazepin-2-one, m.p. 245°–248°C (decomp.), was prepared from 5-(2'-chloro-phenyl)-7-chloro-1,3-dihydro-2H-1,4-benzodiazepin-2-one and piperidino-diethoxy-methane.

EXAMPLE 41

Using a procedure analogous to that described in Example 2, 3-(hexamethyleneimino-methylene)-5-(2'-chloro-phenyl)-7-chloro-1,3-dihydro-2H-1,4-benzodiazepin-2-one, m.p. 238°–239°C, was prepared from 5-(2'-chloro-phenyl)-7-chloro-1,3-dihydro-2H-1,4-benzodiazepin-2-one and hexamethyleneimino-diethoxy-methane.

EXAMPLE 42

Using a procedure analogous to that described in Example 2, 3-(morpholino-methylene)-5-(2'-chloro-phenyl)-7-chloro-1,3-dihydro-2H-1,4-benzodiazepin-2-one, m.p. 209°–211°C, was prepared from 5-(2'-chloro-phenyl)-7-chloro-1,3-dihydro-2H-1,4-benzodiazepin-2-one and morpholino-diethoxy-methane.

EXAMPLE 43

Using a procedure analogous to that described in Example 1, 1-methyl-3-(morpholino-methylene)-5-(2'-chloro-phenyl)-7-chloro-1,3-dihydro-2H-1,4-benzodiazepin-2-one, m.p. 158°–160°C, was prepared from 1-methyl-5-(2'-chloro-phenyl)-7-chloro-1,3-dihydro-2H-1,4-benzodiazepin-2-one and morpholino-diethoxy-methane.

EXAMPLE 44

Using a procedure analogous to that described in Example 1, 1-(cyclopropyl-methyl)-3-(morpholino-methylene)-5-(2'-chloro-phenyl)-7-chloro-1,3-dihydro-2H-1,4-benzodiazepin-2-one, an amorphous foam, of the formula

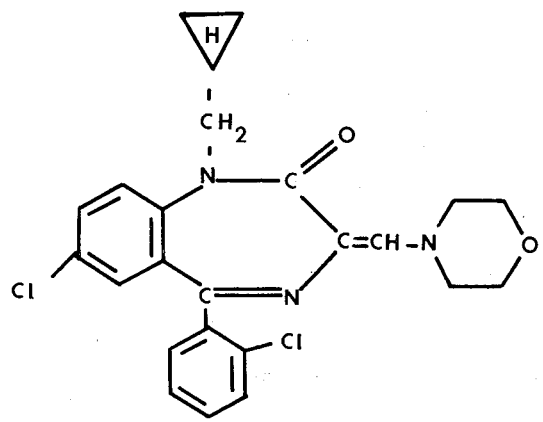

(proof of structure by IR-, UV- and NMR-spectra) was prepared from 1-(cyclopropyl-methyl)-5-(2'-chloro-phenyl)-7-chloro-1,3-dihydro-2H-1,4-benzodiazepin-2-one and morpholino-diethoxy-methane.

EXAMPLE 45

Using a procedure analogous to that described in Example 2, 3-[(N'-methyl-piperazino)-methylene]-5-(2'-chloro-phenyl)-7-chloro-1,3-dihydro-2H-1,4-benzodiazepin-2-one, m.p. 194°–196°C, was prepared from 5-(2'-chloro-phenyl)-7-chloro-1,3-dihydro-2H-1,4-benzodiazepin-2-one and (N'-methyl-piperazino)-diethoxy-methane.

EXAMPLE 46

Using a procedure analogous to that described in Example 1, 1-methyl-3-[(N'-methyl-piperazino)-methylene]-5-(2'-chloro-phenyl)-7-chloro-1,3-dihydro-2H-1,4-benzodiazepin-2-one, an amorphous foam (proof of structure by IR-, UV- and NMR-spectra), was prepared from 1-methyl-5-(2'-chloro-phenyl)-7-chloro-1,3-dihydro-2H-1,4-benzodiazepin-2-one and (N'-methyl-piperazino)-diethoxy-methane.

EXAMPLE 47

Using a procedure analogous to that described in Example 1, 1-methyl-3-(dimethylamino-methylene)-5-(2'-fluorophenyl)-7-chloro-1,3-dihydro-2H-1,4-benzodiazepin-2-one, m.p. 157°–159°C, of the formula

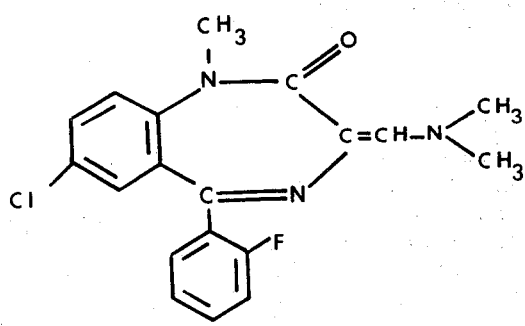

was prepared from 1-methyl-5-(2'-fluoro-phenyl)-7-chloro-1,3-dihydro-2H-1,4-benzodiazepin-2-one and N,N-dimethyl-formamide-diethylacetal.

EXAMPLE 48

Using a procedure analogous to that described in Example 1, 1-methyl-3-(morpholino-methylene)-5-(2'-fluorophenyl)-7-chloro-1,3-dihydro-2H-1,4-benzodiazepin-2-one, m.p. 172°–174°C, was prepared from 1-methyl-5-(2'-fluoro-phenyl)-7-chloro-1,3-dihydro-2H-1,4-benzodiazepin-2-one and morpholino-diethoxy-methane.

EXAMPLE 49

Using a procedure analogous to that described in Example 2, 3-(dimethylamino-methylene)-5-(2'-chloro-phenyl)-7-bromo-1,3-dihydro-2H-1,4-benzodiazepin-2-one, m.p. 220°–223°C, was prepared from 5-(2'-chloro-phenyl)-7-bromo-1,3-dihydro-2H-1,4-benzodiazepin-2-one and N,N-dimethyl-formamide-diethylacetal.

EXAMPLE 50

Using a procedure analogous to that described in Example 1, 1-methyl-3-(diethylamino-methylene)-5-(2'-chlorophenyl)-7-bromo-1,3-dihydro-2H-1,4-benzodiazepin-2-one, m.p. 131°–133°C, was prepared from 1-methyl-5-(2'-chloro-phenyl)-7-bromo-1,3-dihydro-2H-1,4-benzodiazepin-2-one and N,N-diethyl-formamide-diethylacetal.

EXAMPLE 51

Using a procedure analogous to that described in Example 1, 1-methyl-3-(piperidino-methylene)-5-(2'-chlorophenyl)-7-bromo-1,3-dihydro-2H-1,4-benzodiazepin-2-one, m.p. 176°–178°C, was prepared from 1-methyl-5-(2'-chloro-phenyl)-7-bromo-1,3-dihydro-2H-1,4-benzodiazepin-2-one and piperidino-diethoxy-methane.

EXAMPLE 52

Using a procedure analogous to that described in Example 1, 1-methyl-3-(hexamethyleneimino-methylene)-5-(2'-chloro-phenyl)-7-bromo-1,3-dihydro-2H-1,4-benzodiazepin-2-one, m.p. 140°–142°C, was prepared from 1,4-methyl-5-(2'-chloro-phenyl)-7-bromo-1,3-dihydro-2H-1,4-benzodiazepin-2-one and hexamethyleneimino-diethoxy-methane.

EXAMPLE 53

Using a procedure analogous to that described in Example 1, 1-methyl-3-(morpholino-methylene)-5-(2'-chlorophenyl)-7-bromo-1,3-dihydro-2H-1,4-benzodiazepin-2-one, m.p. 148°–153°C, was prepared from 1-methyl-5-(2'-chloro-phenyl)-7-bromo-1,3-dihydro-2H-1,4-benzodiazepin-2-one and morpholino-diethoxy-methane.

EXAMPLE 54

Using a procedure analogous to that described in Example 1, 1-methyl-3-(dimethylamino-methylene)-5-(2'-fluorophenyl)-7-bromo-1,3-dihydro-2H-1,4-benzodiazepin-2-one, m.p. 172°–173°C, was prepared from 1-methyl-5-(2'-fluoro-phenyl)-7-bromo-1,3-dihydro-2H-1,4-benzodiazepin-2-one and N,N-dimethyl-formamide-diethylacetal.

EXAMPLE 55

Using a procedure analogous to that described in Example 2, 3-(dimethylamino-methylene)-5-phenyl-7-nitro-1,3-dihydro-2H-1,4-benzodiazepin-2-one, m.p. 260°–264°C (decomp.), of the formula

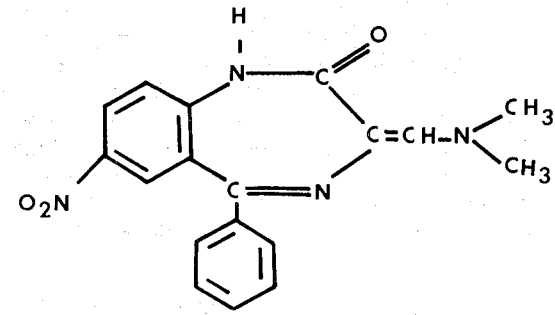

was prepared from 5-phenyl-7-nitro-1,3-dihydro-2H-1,4-benzodiazepin-2-one and N,N-dimethyl-formamide-diethylacetal.

EXAMPLE 56

Using a procedure analogous to that described in Example 1, 1-methyl-3-(dimethylamino-methylene)-5-phenyl-7-nitro-1,3-dihydro-2H-1,4-benzodiazepin-2-one, m.p. 228.5°–229.5°C, was prepared from 1-methyl-5-phenyl-7-nitro-1,3-dihydro-2H-1,4-benzodiazepin-2-one and N,N-dimethyl-formamide-diethylacetal.

EXAMPLE 57

Using a procedure analogous to that described in Example 2, 3-(diallylamino-methylene)-5-phenyl-7-nitro-1,3-dihydro-2H-1,4-benzodiazepin-2-one, m.p. 194°–195°C, was prepared from 5-phenyl-7-nitro-1,3-dihydro-2H-1,4-benzodiazepin-2-one and N,N-diallyl-formamide-diethylacetal.

EXAMPLE 58

Using a procedure analogous to that described in Example 1, 3-[N-(β-dimethylamino-ethyl)-N-methyl-aminomethylene]-5-phenyl-7-nitro-1,3-dihydro-2H-1,4-benzodiazepin-2-one, m.p. 200°–202°C, was prepared from 5-phenyl-7-nitro-1,3-dihydro-2H-1,4-benzodiazepin-2-one and [N-(β-dimethylamino-ethyl)-N-methyl-formamide]-diethylacetal.

EXAMPLE 59

Using a procedure analogous to that described in Example 2, 3-(morpholino-methylene)-5-phenyl-7-nitro-1,3-dihydro-2H-1,4-benzodiazepin-2-one, m.p. 243°–245°C (decomp.), was prepared from 5-phenyl-7-nitro-1,3-dihydro-2H-1,4-benzodiazepin-2-one and morpholino-diethoxy-methane.

EXAMPLE 60

Using a procedure analogous to that described in Example 2, 1-methyl-3-(morpholino1-methylene)-5-phenyl-7-nitro-1,3-dihydro-2H-1,4-benzodiazepin-2-one, m.p. 211°–212°C, was prepared from 1-methyl-5-phenyl-7-nitro-1,3-dihydro-2H-1,4-benzodiazepin-2-one and morpholino-diethoxy-methane.

EXAMPLE 61

Using a procedure analogous to that described in Example 2, 3-(dimethylamino-methylene)-5-(2'-chloro-phenyl)-7-nitro-1,3-dihydro-2H-1,4-benzodiazepin-2-one, m.p. 241°C (decomp.), was prepared from 5-(2'-chloro-phenyl)-7-nitro-1,3-dihydro-2H-1,4-benzodiazepin-2-one and N,N-dimethylformamide-diethylacetal.

EXAMPLE 62

Using a procedure analogous to that described in Example 2, 3-(diethylamino-methylene)-5-(2'-chloro-phenyl)-7-nitro-1,3-dihydro-2H-1,4-benzodiazepin-2-one, m.p. 208°–209°C, was prepared from 5-(2'-chloro-phenyl)-7-nitro-1,3-dihydro-2H-1,4-benzodiazepin-2-one and N,N-diethyl-formamidediethylacetal.

EXAMPLE 63

Using a procedure analogous to that described in Example 1, 1-methyl-3-(diethylamino-methylene)-5-(2'-chlorophenyl)-7-nitro-1,3-dihydro-2H-1,4-benzodiazepin-2-one, m.p. 148°–150°C, was prepared from 1-methyl-5-(2'-chloro-phenyl)-7-nitro-1,3-dihydro-2H-1,4-benzodiazepin-2-one and N,N-dimethyl-formamide-diethylacetal.

EXAMPLE 64

Using a procedure analogous to that described in Example 2, 3-(di-n-propylamino-methylene)-5-(2'-chloro-phenyl)-7-nitro-1,3-dihydro-2H-1,4-benzodiazepin-2-one, m.p. 241°–242°C, was prepared from 5-(2'-chloro-phenyl)-7-nitro-1,3-dihydro-2H-1,4-benzodiazepin-2-one and N,N-di-n-propylformamide-diethylacetal.

EXAMPLE 65

Using a procedure analogous to that described in Example 1, 1-methyl-3-(di-n-propylamino-methylene)-5-(2'-chloro-phenyl)-7-nitro-1,3-dihydro-2H-1,4-benzodiazepin-2-one, m.p. 71°–75°C, was prepared from 1-methyl-5-(2'-chlorophenyl)-7-nitro-1,3-dihydro-2H-1,4-benzodiazepin-2-one and N,N-di-n-propyl formamide-diethylacetal.

EXAMPLE 66

Using a procedure analogous to that described in Example 2, 3-(diallylamino-methylene)-5-(2'-chloro-phenyl)-7-nitro-1,3-dihydro-2H-1,4-benzodiazepin-2-one, m.p. 179°–181°C, was prepared from 5-(2'-chloro-phenyl)-7-nitro-1,3-dihydro-2H-1,4-benzodiazepin-2-one and N,N-diallyl-formamide-diethylacetal.

EXAMPLE 67

Using a procedure analogous to that described in Example 1, 1-methyl-3-(diallylamino-methylene)-5-(2'-chlorophenyl)-7-nitro-1,3-dihydro-2H-1,4-benzodiazepin-2-one, m.p. 55°–60°C, was prepared from 1-methyl-5-(2'-chloro-phenyl)-7-nitro-1,3-dihydro-2H-1,4-benzodiazepin-2-one and N,N-diallyl-formamide-diethylacetal.

EXAMPLE 68

Using a procedure analogous to that described in Example 2, 3-(diisopropylamino-methylene)-5-(2'-chloro-phenyl)-7-nitro-1,3-dihydro-2H-1,4-benzodiazepin-2-one, m.p. 211°–213°C, was prepared from 5-(2'-chloro-phenyl)-7-nitro-1,3-dihydro-2H-1,4-benzodiazepin-2-one and N,N-diisopropyl-formamide-diethylacetal.

EXAMPLE 69

Using a procedure analogous to that described in Example 1, 1-methyl-3-(diisopropylamino-methylene)-5-(2'-chloro-phenyl)-7-nitro-1,3-dihydro-2H-1,4-benzodiazepin-2-one, m.p. 156°–158°C, was prepared from 1-methyl-5-(2'-chlorophenyl)-7-nitro-1,3-dihydro-2H-1,4-benzodiazepin-2-one and N,N-diisopropyl-formamide-diethylacetal.

EXAMPLE 70

Using a procedure analogous to that described in Example 2, 3-[(N-cyclohexyl-N-methyl-amino)-methylene]-5-(2'-chloro-phenyl)-7-nitro-1,3-dihydro-2H-1,4-benzodiazepin-2-one, m.p. 209°–211°C, was prepared from 5-(2'-chloro-phenyl)-7-nitro-1,3-dihydro-2H-1,4-benzodiazepin-2-one and (N-cyclohexyl-N-methyl-formamide)-diethylacetal.

EXAMPLE 71

Using a procedure analogous to that described in Example 1, 1-methyl-3-[(N-cyclohexyl-N-methyl-amino)-methylene]-5-(2'-chloro-phenyl)-7-nitro-1,3-dihydro-2H-1,4-benzodiazepin-2-one, m.p. 107°–109°C, was prepared from 1-methyl-5-(2'-chloro-phenyl)-7-nitro-1,3-dihydro-2H-1,4-benzodiazepin-2-one and (N-cyclohexyl-N-methyl-formamide)-diethylacetal.

EXAMPLE 72

Using a procedure analogous to that described in Example 1, 1-methyl-3-[(N-methyl-anilino)-methylene]-5-(2'-chloro-phenyl)-7-nitro-1,3-dihydro-2H-1,4-benzodiazepin-2-one, m.p. 183°–185°C, was prepared from 1-methyl-5-(2'-chloropheny)-7-nitro-1,3-dihydro-2H-1,4-benzodiazepin-2-one and (N-methyl-N-phenyl-formamide)-diethylacetal.

EXAMPLE 73

Using a procedure analogous to that described in Example 2, 3-(pyrrolidino-methylene)-5-(2'-chlorophenyl)-7-nitro-1,3-dihydro-2H-1,4-benzodiazepin-2-one, m.p. 251°–252°C, was prepared from 5-(2'-chloro-phenyl)-7-nitro-1,3-dihydro-2H-1,4-benzodiazepin-2-one and pyrrolidino-diethoxy-methane.

EXAMPLE 74

Using a procedure analogous to that described in Example 1, 1-methyl-3-(pyrrolidino-methylene)-5-(2'-chlorophenyl)-7-nitro-1,3-dihydro-2H-1,4-benzodiazepin-2-one, m.p. 184°–185°C, was prepared from 1-methyl-5-(2'-chloro-phenyl)-7-nitro-1,3-dihydro-2H-1,4-benzodiazepin-2-one and pyrrolidino-diethoxymethane.

EXAMPLE 75

Using a procedure analogous to that described in Example 1, 1-methyl-3-(piperidino-methylene)-5-(2'-chlorophenyl)-7-nitro-1,3-dihydro-2H-1,4-benzodiazepin-2-one, m.p. 139°–141°C, was prepared from 1-methyl-5-(2'-chloro-phenyl)-7-nitro-1,3-dihydro-2H-1,4-benzodiazepin-2-one and piperidino-diethoxymethane.

EXAMPLE 76

Using a procedure analogous to that described in Example 2, 3-(piperidino-methylene)-5-(2'-chlorophenyl)-7-nitro-1,3-dihydro-2H-1,4-benzodiazepin-2-one, m.p. 235°–236°C, was prepared from 5-(2'-chloro-phenyl)-7-nitro-1,3-dihydro-2H-1,4-benzodiazepin-2-one and piperidino-diethoxy-methane.

EXAMPLE 77

Using a procedure analogous to that described in Example 2, 3-(hexamethyleneimino-methylene)-5-(2'-chlorophenyl)-7-nitro-1,3-dihydro-2H-1,4-benzodiazepin-2-one, m.p. 217°–218°C, was prepared from 5-(2'-chloro-phenyl)-7-nitro-1,3-dihydro-2H-1,4-benzodiazepin-2-one and hexamethyleneimino-diethoxymethane.

EXAMPLE 78

Using a procedure analogous to that described in Example 2, 3-(morpholino-methylene)-5-(2'-chlorophenyl)-7-nitro-1,3-dihydro-2H-1,4-benzodiazepine-2-one, m.p. 246°–248°C, was prepared from 5-(2'-chloro-phenyl)-7-nitro-1,3-dihydro-2H-1,4-benzodiazepin-2-one and morpholino-diethoxy-methane.

EXAMPLE 79

Using a procedure analogous to that described in Example 2, 3-(dimethylamino-methylene)-5-(2'-fluoro-phenyl)-7-nitro-1,3-dihydro-2H-1,4-benzodiazepin-2-one, m.p. 243°–244°C (decomp.), was prepared from 5-(2'-fluoro-phenyl)-7-nitro-1,3-dihydro-2H-1,4-benzodiazepin-2-one and N,N-dimethyl-formamide-diethylacetal.

EXAMPLE 80

Using a procedure analogous to that described in Example 2, 1-methyl-3-(dimethylamino-methylene)-5-(2'-fluoro-phenyl)-7-nitro-1,3-dihydro-2H-1,4-benzodiazepin-2-one, m.p. 193°–194.5°C, was prepared from 1-methyl-5-(2'-fluoro-phenyl)-7-nitro-1,3-dihydro-2H-1,4-benzodiazepin-2-one and N,N-dimethyl-formamide-diethylacetal.

EXAMPLE 81

Using a procedure analogous to that described in Example 2, 3-(diallylamino-methylene)-5-(2'-fluoro-phenyl)-7-nitro-1,3-dihydro-2H-1,4-benzodiazepin-2-one, m.p. 201°–202°C, was prepared from 5-(2'-fluoro-phenyl)-7-nitro-1,3-dihydro-2H-1,4-benzodiazepin-2-one and N,N-diallyl-formamide-diethylacetal.

EXAMPLE 82

Using a procedure analogous to that described in Example 2, 3-(morpholino-methylene)-5-(2'-fluoro-phenyl)-7-nitro-1,3-dihydro-2H-1,4-benzodiazepin-2-one, m.p. 246°–249°C (decomp.), was prepared from 5-(2'-fluoro-phenyl)-7-nitro-1,3-dihydro-2H-1,4-benzodiazepin-2-one and morpholino-diethoxy-methane.

EXAMPLE 83

Using a procedure analogous to that described in Example 2, 1-methyl-3-(morpholino-methylene)-5-(2'-fluorophenyl)-7-nitro-1,3-dihydro-2H-1,4-benzodiazepin-2-one, m.p. 187°–188°C, was prepared from 1-methyl-5-(2'-fluoro-phenyl)-7-nitro-1,3-dihydro-2H-1,4-benzodiazepin-2-one and morpholino-diethoxymethane.

EXAMPLE 84

Using a procedure analogous to that described in Example 3, 3-(amino-methylene)-5-phenyl-7-chloro-1,3-dihydro-2H-1,4-benzodiazepine-2-one, m.p. 244°–247°C, of the formula

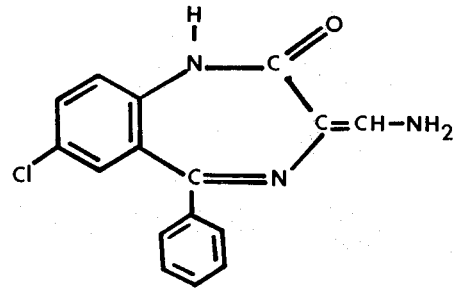

was prepared from 3-(dimethylamino-methylene)-5-phenyl-7-chloro-1,3-dihydro-2H-1,4-benzodiazepin-2-one and ammonia.

EXAMPLE 85

Using a procedure analogous to that described in Example 3, 1-methyl-3-(amino-methylene)-5-phenyl-7-chloro-1,3-dihydro-2H-1,4-benzodiazepin-2-one, an amorphous foam (proof of structure by IR-, UV-, and NMR-spectra), was prepared from 1-methyl-3-(dimethylamino-methylene)-5-phenyl-7-chloro-1,3-dihydro-2H-1,4-benzodiazepin-2-one and ammonia.

EXAMPLE 86

Using a procedure analogous to that described in Example 3, 3-(methylamino-methylene)-5-phenyl-7-chloro-1,3-dihydro-2H-1,4-benzodiazepin-2-one, m.p. 210°C, of the formula

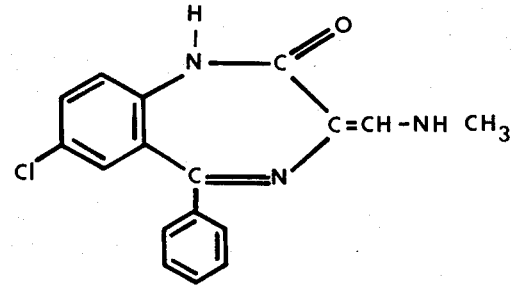

was prepared from 3-(dimethylamino-methylene)-5-phenyl-7-chloro-1,3-dihydro-2H-1,4-benzodiazepin-2-one and methylamine.

EXAMPLE 87

Using a procedure analogous to that described in Example 3, 3-(ethanolamino-methylene)-5-phenyl-7-chloro-1,3-dihydro-2H-1,4-benzodiazepin-2-one, m.p. 228°–230°C, of the formula

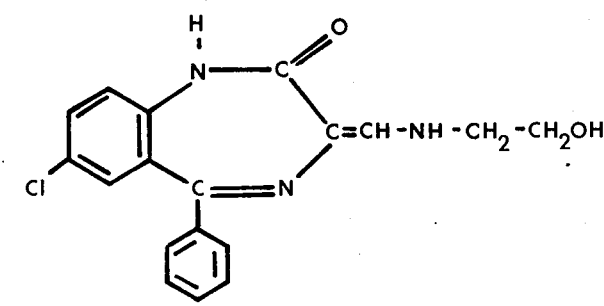

was prepared from 3-(dimethylamino-methylene)-5-phenyl-7-chloro-1,3-dihydro-2H-1,4-benzodiazepin-2one and ethanolamine.

EXAMPLE 88

Using a procedure analogous to that described in Example 3, 1-methyl-3-(ethanolamino-methylene)-5-phenyl-7-chloro-1,3-dihydro-2H-1,4-benzodiazepin-2-one, an amorphous foam (proof of structure by IR-, UV- and NMR-spectra), was prepared from 1-methyl-3-(dimethylamino-methylene)-5-phenyl-7-chloro-1,3-dihydro-2H-1,4-benzodiazepin-2-one and ethanolamine.

EXAMPLE 89

Using a procedure analogous to that described in Example 3 1-methyl-3-[N-(β-diethylamino-ethyl)-amino-methylene]-5-phenyl-7-chloro-1,3-dihydro-2H-1,4-benzodiazepin-2-one, an amorphous foam, of the formula

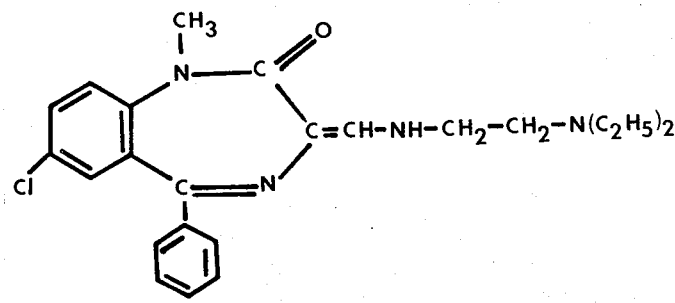

(proof of structure by IR-, UV- and NMR-spectra) was prepared from 1-methyl-3-(dimethylamino-methylene)-5-phenyl-7-chloro-1,3-dihydro-2H-1,4-benzodiazepin-2-one and N-(β-diethy(amino-ethyl)-amine.

EXAMPLE 90

Using a procedure analogous to that described in Example 3, 1-methyl-3-(n-butylamino-methylene)-5-phenyl-7-chloro-1,3-dihydro-2H-1,4-benzodiazepin-2-one, an amorphous foam (proof of structure by IR-, UV- and NMR-spectra), was prepared from 1-methyl-3-(dimethylamino-methylene)-5-phenyl-7-chloro-1,3-dihydro-2H-1,4-benzodiazepin-2-one and n-butylamine.

EXAMPLE 91

Using a procedure analogous to that described in Example 3, 3-(ethylamino-methylene)-5-(2'-fluorophenyl)-7-nitro-1,3-dihydro-2H-1,4-benzodiazepin-2-one, m.p. 240°–241°C, was prepared from 3-(dimethylamino-methylene)-5-(2'-fluorophenyl)-7-nitro-1,3-dihydro-2H-1,4-benzodiazepin-2-one and ethylamine.

EXAMPLE 92

Using a procedure analogous to that described in Example 3, 1-methyl-3-(ethylamino-methylene)-5(2'-fluorophenyl)-7-nitro-1,3-dihydro-2H-1,4-benzodiazepin-2-one, m.p. 175°–176.5°C, was prepared from 1-methyl-3-(dimethylaminomethylene)-5-(2'-fluorophenyl)-7-nitro-1,3-dihydro-2H-1,4-benzodiazepin-2-one and ethylamine.

EXAMPLE 93

Using a procedure analogous to that described in Example 3, 3-(amino-methylene)-5-(2'-chloro-phenyl)-7-chloro-1,3-dihydro-2H-1,4-benzodiazepin-2-one, m.p. 220–222°C, was prepared from 3-(dimethylamino-methylene)-5-(2'-chloro-phenyl)-7-chloro-1,3-dihydro-2H-1,4-benzodiazepin-2-one and ammonia.

EXAMPLE 94

Using a procedure analogous to that described in Example 3, 1-methyl-3-(amino-methylene)-5-(2'-chloro-phenyl)-7-chloro-1,3-dihydro-2H-1,4-benzodiazepin-2-one, m.p. 201°–204°C, was prepared from 1-methyl-(3-dimethylamino-methylene)-5-(2'-chloro-phenyl)-7-chloro-1,3-dihydro-2H-1,4-benzodiazepin-2-one and ammonia.

EXAMPLE 95

Using a procedure analogous to that described in Example 3, 3-(methylamino-methylene)-5-(2'-chloro-phenyl)-7-chloro-1,3-dihydro-2H-1,4-benzodiazepin-2-one, m.p. 225°C, was prepared from 3-(dimethyamino-methylene)-5-(2'-chlorophenyl)-7-chloro-1,3-dihydro-2H-1,4-benzodiazepin-2-one and methylamine.

EXAMPLE 96

Using a procedure analogous to that described in Example 3, 1-methyl-3-(ethylamino-methylene)-5-(2'-chlorophenyl)-7-chloro-1,3-dihydro-2H-1,4-benzodiazepin-2-one, m.p. 122°C, was prepared from 1-methyl-3-(dimethylamino-methylene)-5-(2'-chlorophenyl)-7-chloro-1,3-dihydro-2H-1,4-benzodiazepin-2-one and ethylamine.

EXAMPLE 97

Using a procedure analogous to that described in Example 3, 3-(n-propylamino-methylene)-5-(2'-chloro-phenyl)-7-chloro-1,3-dihydro-2H-1,4-benzodiazepin-2-one, m.p. 186°C, was prepared from 3-(dimethylamino-methylene)-5-(2'-chlorophenyl)-7-chloro-1,3-dihydro-2H-1,4-benzodiazepin-2-one and n-propylamine.

EXAMPLE 98

Using a procedure analogous to that described in Example 3, 1-methyl-3-(n-propylamino-methylene)-5-(2'-chloro-phenyl)-7-chloro-1,3-dihydro-2H-1,4-benzodiazepin-2-one, m.p. 146°–147°C, was prepared from 1-methyl-3-(dimethylaminomethylene)-5-(2'-chloro-phenyl)-7-chloro-1,3-dihydro-2H-1,4-benzodiazepin-2-one and n-propylamine.

EXAMPLE 99

Using a procedure analogous to that described in Example 3, 3-(isopropylamino-methylene)-5-(2'-chloro-phenyl)-7-chloro-1,3-dihydro-2H-1,4-benzodiazepin-2-one, m.p. 188°–191°C, was prepared from 3-(dimethylamino-methylene)-5-(2'-chloro-phenyl)-7-chloro-1,3-dihydro-2H-1,4-benzodiazepin-2-one and isopropylamine.

EXAMPLE 100

Using a procedure analogous to that described in Example 3, 3-(n-butylamino-methylene)-5-(2'-chloro-phenyl)-7-chloro-1,3-dihydro-2H-1,4-benzodiazepin-2-one, m.p. 173°C, was prepared from 3-(dimethylamino-methylene)-5-(2'-chloro-phenyl)-7-chloro-1,3-dihydro-2H-1,4-benzodiazepin-2-one and n-butylamine.

EXAMPLE 101

Using a procedure analogous to that described in Example 3, 1-methyl-3-(n-butylamino-methylene)-5-(2'-chlorophenyl)-7-chloro-1,3-dihydro-2H-1,4-benzodiazepin-2-one, m.p. 110°–113°C, was prepared from 1-methyl-3-(dimethylamino-methylene)-5-(2'-chlorophenyl)-7-chloro-1,3-dihydro-2H-1,4-benzodiazepin-2-one and n-butylamine.

EXAMPLE 102

Using a procedure analogous to that described in Example 3, 3-(tert.butylamino-methylene)-5-(2'-chloro-phenyl)-7-chloro-1,3-dihydro-2H-1,4-benzodiazepin-2-one, m.p. 230°C, was prepared from 3-(dimethylamino-methylene)-5-(2'-chloro-phenyl)-7-chloro-1,3-dihydro-2H-1,4-benzodiazepin-2-one and tert, butylamine.

EXAMPLE 103

Using a procedure analogous to that described in Example 3, 1-methyl-3-(tert.butylamino-methylene)-5-(2'-chloro-phenyl)-7-chloro-1,3-dihydro-2H-1,4-benzodiazepin-2-one, m.p. 175°–177°C, was prepared from 1-methyl-3-(dimethylamino-methylene)-5-(2'-chlorophenyl)-7-chloro-1,3-dihydro-2H-1,4-benzodiazepin-2-one and tert.butylamine.

EXAMPLE 104

Using a procedure analogous to that described in Example 3, 3-(ethanolamino-methylene)-5-(2'-chlorophenyl)-7-chloro-1,3-dihydro-2H-1,4-benzodiazepin-2-one, m.p. 231°–233°C, was prepared from 3-(dimethylamino-methylene)-5-(2'-chlorophenyl)-7-chloro-1,3-dihydro-2H-1,4-benzodiazepin-2-one and ethanolamine.

EXAMPLE 105

Using a procedure analogous to that described in Example 3, 1-methyl-3-(ethanolamino-methylene)-5-(2'-chlorophenyl)-7-chloro-1,3-dihydro-2H-1,4-benzodiazepin-2-one, m.p. 155°–157°C, was prepared from 1-methyl-3-(dimethyaminomethylene)-5-(2'-chlorophenyl)-7-chloro-1,3-dihydro-2H-1,4-benzodiazepin-2-one and ethanolamine.

EXAMPLE 106

Using a procedure analogous to that described in Example 3, 3-[N-($\beta$-diethylamino-ethyl)-aminomethylene]-5-(2'-chloro-phenyl)-7-chloro-1,3-dihydro-2H-1,4-benzodiazepin-2-one, an amorphous foam (proof of structure by IR-, UV- and NMR-spectra), was prepared from 3-(dimethylamino-methylene)-5-(2'-chloro-phenyl)-7-chloro-1,3-dihydro-2H-1,4-benzodiazepin-2-one and N-($\beta$-diethylamino-ethyl)-amine.

EXAMPLE 107

Using a procedure analogous to that described in Example 3, 1-methyl-3-[N-($\beta$-diethylamino-ethyl)-amino-methylene]-5-(2'-chloro-phenyl)-7-chloro-1,3-dihydro-2H-1,4-benzodiazepin-2-one, an amorphous foam (proof of structure by IR-, UV- and NMR-spectra), was prepared from 1-methyl-3-(dimethylamino-methylene)-5-(2'-chloro-phenyl)-7-chloro-1,3-dihydro-2H-1,4-benzodiazepin-2-one and N-($\beta$-diethylamino-ethyl)-amine.

EXAMPLE 108

Using a procedure analogous to that described in Example 3, 1-methyl-3-(ethylamino-methylene)-5-(2'-fluorophenyl)-7-chloro-1,3-dihydro-2H-1,4-benzodiazepin-2-one, m.p. 151°–154°C, was prepared from 1-methyl-3-(dimethylamino-methylene)-5-(2'-fluorophenyl)-7-chloro-1,3-dihydro-2H-1,4-benzodiazepin-2-one and ethylamine.

EXAMPLE 109

Using a procedure analogous to that described in Example 3, 1-methyl-3-(amino-methylene)-5-(2'-chloro-phenyl)-7-bromo-1,3-dihydro-2H-1,4-benzodiazepin-2-one, an amorphous substance which decomposed slowly between 80° and 110°C (proof of structure by IR-, UV- and NMR-spectra), m.p. 186°–189.5°C (decomp., recrystallized from ether), was prepared from 1-methyl-3-(dimethylaminomethylene)-5-(2'-chloro-phenyl)-7-bromo-1,3-dihydro-2H-1,4-benzodiazepin-2-one and ammonia.

EXAMPLE 110

Using a procedure analogous to that described in Example 3, 1-methyl-3-(ethylamino-methylene)-5-(2'- chlorophenyl)-7-bromo-1,3-dihydro-2H-1,4-benzodiazepin-2-one, m.p. 173°–175°C, was prepared from 1-methyl-3-(dimethylamino-methylene)-5-(2'-chlorophenyl)-7-bromo-1,3-dihydro-2H-1,4-benzo-diazepin-2-one and ethylamine.

EXAMPLE 111

Using a procedure analogous to that described in Example 3, 1-methyl-3-(n-butylamino-methylene)-5-(2'-chlorophenyl)-7-bromo-1,3-dihydro-2H-1,4-benzodiazepin-2-one, m.p. 142°–145°C, was prepared from 1-methyl-3-(dimethylamino-methylene)-5-(2'-chlorophenyl)-7-bromo-1,3-dihydro-2H-1,4-benzodiazepin-2-one and n-butylamine.

EXAMPLE 112

Using procedure analogous to that described in Example 3, 1-methyl-3-(cyclopropylamino-methylene)-5-(2'-chloro-phenyl)-7-bromo-1,3-dihydro-2H-1,4-benzodiazepin-2-one, m.p. 136°–138°C (decomp.), of the formula

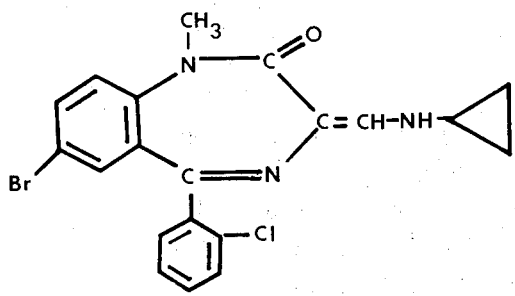

was prepared from 1-methyl-3-(dimethylamino-methylene)-5-(2'-chloro-phenyl)-7-bromo-1,3-dihydro-2H-,1,4-benzodiazepin-2-one and cyclopropylamine.

EXAMPLE 113

Using a procedure analogous to that described in Example 3, 1-methyl-3-[N-(ethoxycarbonyl-methyl)-amino-methylene]-5-(2'-chloro-phenyl)-7-bromo-1,3-dihydro-2H-1,4-benzodiazepin-2-one, m.p. 175°–177°C, of the formula

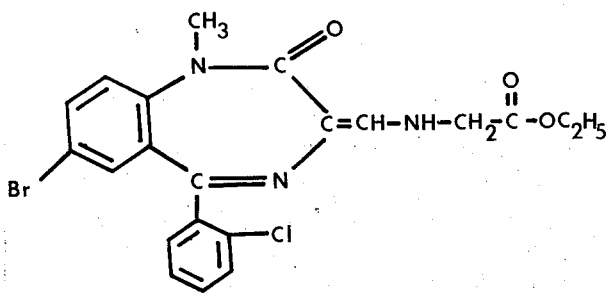

was prepared from 1-methyl-3-(dimethylamino-methylene)-5-(2'-chloro-phenyl)-7-bromo-1,3-dihydro-2H-1,4-benzodiazepin-2-one and glycine ethyl ester.

EXAMPLE 114

Using a procedure analogous to that described in Example 3, 1-methyl-3-[(β-furfuryl-amino)-methylene]-5-(2'-chloro-phenyl)-7-bromo-1,3-dihydro-2H-1,4-benzodiazepin-2-one, m.p. 81°–83°C, of the formula

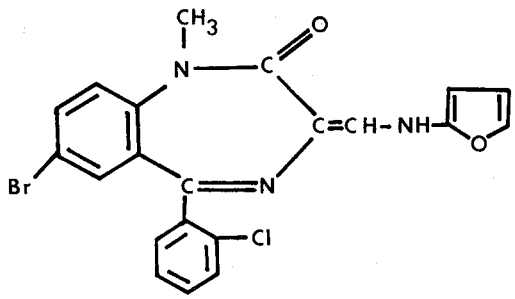

was prepared from 1-methyl-3-(dimethylamino-methylene)-5-(2'-chloro-phenyl)-7-bromo-1,3-dihydro-2H-1,4-benzodiazepin-2-one and α-furfurylamine

EXAMPLE 115

Using a procedure analogous to that described in Example 3, 3-(ethylamino-methylene)-5-(2'-chlorophenyl)-7-nitro-1,3-dihydro-2H-1,4-benzodiazepin-2-one, m.p. 260°–261°C, was prepared from 3-(dimethylamino-methylene)-5-(2'-chlorophenyl)-7-nitro-1,3-dihydro-2H-1,4-benzodiazepin-2-one and ethylamine.

EXAMPLE 116

Using a procedure analogous to that described in Example 3, 3-(n-butylamino-methylene)-5-(2'-chlorophenyl)-7-nitro-1,3-dihydro-2H-1,4-benzodiazepin-2-one, m.p. 222°–224°C, was prepared from 3-(dimethylamino-methylene)-5-(2'-chloro-phenyl)-7-nitro-1,3-dihydro-2H-1,4-benzodiazepin-2-one and n-butylamine.

EXAMPLE 117

Using a procedure analogous to that described in Example 3, 3-[N-(β-dimethylamino-ethyl)-aminomethylene]-5-(2'-chloro-phenyl)-7-nitro-1,3-dihydro-2H-1,4-benzodiazepin-2-one, m.p. 164–165°C, was prepared from 3-(dimethylaminomethylene)-5-(2'-chloro-phenyl)-7-nitro-1,3-dihydro-2H-1,4-benzodiazepin-2-one and N-(β-diethylamino-ethyl)-amine.

EXAMPLE 118

Using a procedure analogous to that described in Example 4, 1-(β-dimethylamino-ethyl)-3-(pyrrolidinomethylene)-5-phenyl-7-chloro-1,3-dihydro-2H-1,4-benzodiazepin-2-one, m.p. 139°–141°C, of the formula

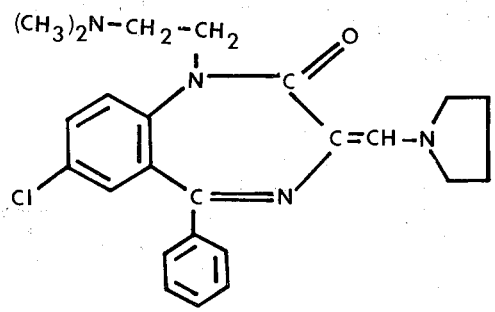

was prepared from 3-(pyrrolidino-methylene)-5-phenyl-7-chloro-1,3-dihydro-2H-1,4-benzodiazepin-2-one and β-dimethylamino-ethyl chloride.

EXAMPLE 119

Using a procedure analogous to that described in Example 4, 1-(β-dimethylamino-ethyl)-3-(dimethylamino-methylene)-5-(2'-chloro-phenyl)-7-chloro-1,3-dihydro-2H-1,4-benzodiazepin-2-one, an amorphous foam (proof of structure by IR-, UV- and NMR-spectra), was prepared from 3-(dimethylamino-methylene)-5-(2'-chloro-phenyl)-7-chloro-1,3-dihydro-2H-1,4-benzodiazepin-2-one and β-dimethylamino-ethyl chloride.

EXAMPLE 120

Using a procedure analogous to that described in Example 4, 1-(cyclopropyl-methyl)-3-(dimethylamino-methylene)-5-(2'-chloro-phenyl)-7-chloro-1,3-dihydro-2H-1,4-benzodiazepin-2-one, m.p. 188°–190°C, was prepared from 3-(dimethylamino-methylene)-5-(2'-chloro-phenyl)-7-chloro-1,3-dihydro-2H-1,4-benzodiazepin-2-one and cyclopropyl-methyl chloride.

EXAMPLE 121

Using a procedure analogous to that described in Example 4, 1-methyl-3-(diethylamino-methylene)-5-(2'-chlorophenyl)-7-chloro-1,3-dihydro-2H-1,4-benzodiazepin-2-one, m.p. 135°–137°C, was prepared from 3-(diethylamino-methylene)-5-(2'-chloro-phenyl)-7-chloro-1,3-dihydro-2H-1,4-benzodiazepin-2-one and methyl iodide.

EXAMPLE 122

Using a procedure analogous to that described in Example 4, 1-methyl-3-(di-n-propylamino-methylene)-5-(2'-chloro-phenyl)-7-chloro-1,3-dihydro-2H-1,4-benzodiazepin-2-one, m.p. 130°–132°C, was prepared from 3-(di-n-propylaminoethylene)-5-(2'-chloro-phenyl)-7-chloro-1,3-dihydro-2H-1,4-benzodiazepin-2-one and methyl iodide.

EXAMPLE 123

Using a procedure analogous to that described in Example 4, 1-methyl-3-(diallylamino-methylene)-5-(2'-chlorophenyl)-7-chloro-1,3-dihydro-2H-1,4-benzodiazepin-2-one, an amorphous foam (proof of structure by IR-, UV- and NMR-spectra), was prepared from 3-(diallylamino-methylene)-5-(2'-chloro-phenyl)-7-chloro-1,3-dihydro-2H-1,4-benzodiazepin-2-one and methyl iodide.

EXAMPLE 124

Using a procedure analogous to that described in Example 4, 1-methyl-3-(diisopropylamino-methylene)-5-(2'-chloro-phenyl)-7-chloro-1,3-dihydro-2H-1,4-benzodiazepin-2-one, m.p. 147°–149°C, was prepared from 3-(diisopropylaminomethylene)-5-(2'-chloro-phenyl)-7-chloro-1,3-dihydro-2H-1,4-benzodiazepin-2-one and methyl iodide.

EXAMPLE 125

Using a procedure analogous to that described in Example 4, 1-methyl-3-(di-n-butylamino-methylene)-5-(2'-chloro-phenyl)-7-chloro-1,3-dihydro-2H-1,4-benzodiazepin-2-one, an amorphous foam (proof of structure by IR-, UV- and NMR-spectra), was prepared from 3-(n-butylamino-methylene)-5-(2'-chloro-phenyl)-7-chloro-1,3-dihydro-2H-1,4-benzodiaze-pin-2-one and methyl iodide.

EXAMPLE 126

Using a procedure analogous to that described in Example 4, 1-methyl-3-[(N-cyclohexyl-N-methyl-amino)-methylene]-5-(2'-chloro-phenyl)-7-chloro-1,3-dihydro-2H-1,4-benzodiazepin-2-one, m.p 170°–172°C, was prepared from 3-[(N-cyclo-hexyl-N-methyl-amino)-methylene]-5-(2'-chloro-phenyl)-7-chloro-1,3-dihydro-2H-1,4-benzodiazepin-2-one and methyl iodide.

EXAMPLE 127

Using a procedure analogous to that described in Example 4, 1-methyl-3-(pyrrolidino-methylene)-5-(2'-chlorophenyl)-7-chloro-1,3-dihydro-2H-1,4-benzodiazepin-2-one, m.p. 181°–183°C, was prepared from 3-(pyrrolidino-methylene)-5-(2'-chloro-phenyl)-7-chloro-1,3-dihydro-2H-1,4-benzodiazepin-2-one and methyl iodide.

EXAMPLE 128

Using a procedure analogous to that described in Example 4, 1-methyl-3-(piperidino-methylene)-5-(2'-chlorophenyl)-7-chloro-1,3-dihdydro-2H-1,4-benzodiazepin-2-one, an amorphous foam (proof of structure by IR-, UV- and NMR-spectra), was prepared from 3-(piperidino-methylene)-5-(2'-chloro-phenyl)-7-chloro-1,3-dihydro-2H-1,4-benzodiazepin-2-one and methyl iodide.

EXAMPLE 129

Using a procedure analogous to that described in Example 4, 1-methyl-3-(hexamethyleneimino-methylene)-5-(2'-chloro-phenyl)-7-chloro-1,3-dihydro-2H-1,4-benzodiazepin-2-one, an amorphous foam (proof of structure by IR-, UV- and spectra), was prepared from 3-(hexamethyleneimino-methylene)-5-(2'-chloro-phenyl)-7-chloro-1,3-dihydro-2H-1,4-benzodiazepin-2-one and methyl iodide.

EXAMPLE 130

Using a procedure analogous to that described in Example 4, 1-methyl-3-(morpholino-methylene)-5-(2'-chlorophenyl)-7-chloro-1,3-dihydro-2H-1,4-benzodiazepin-2-one, m.p. 153°–155°C, was prepared from 3-(morpholino-methylene)-5-(2'-chloro-phenyl)-7-chloro-1,3-dihydro-2H-1,4-benzodiazepin-2-one and methyl iodide.

EXAMPLE 131

Using a procedure analogous to that described in Example 4, 1-methyl-3-(dimethylamino-methylene)-5-(2'-chloro-phenyl)-7-bromo-1,3-dihydro-2H-1,4-benzodiazepin-2-one, m.p. 198°–199°C, was prepared from 3-(dimethylamino-methylene)-5-(2'-chloro-phenyl)-7-bromo-1,3-dihydro-2H-1,4-benzodiazepin-2-one and methyl iodide.

EXAMPLE 132

Using a procedure analogous to that described in Example 4, 1-methyl-3-(ethylamino-methylene)-5-(2'-chloro-phenyl)-7-nitro-1,3-dihydro-2H-1,4-benzodiazepin-2-one, m.p. 159°–161°C, was prepared from 3-(ethylamino-methylene)-5-(2'-chloro-phenyl)-7-nitro-1,3-dihydro-2H-1,4-benzodiazepin-2-one and methyl iodide.

EXAMPLE 133

Using a procedure analogous to that described in Example 4, 1-methyl-3-(n-butylamino-methylene)-5-(2'-chloro-phenyl)-7-nitro-1,3-dihydro-2H-1,4-benzodiazepin-2-one, m.p. 90°C (decomp.), was prepared from 3-(n-butylamino-methylene)-5-(2'-chloro-phenyl)-7-nitro-1,3-dihydro-2H-1,4-benzodiazepin-2-one and methyl iodide.

EXAMPLE 134

Using a procedure analogous to that described in Example 4, 1-methyl-3-(dimethylamino-methylene)-5-(2'-chloro-phenyl)-7-nitro-1,3-dihydro-2H-1,4-benzodiazepin-2-one, m.p. 182–183°C, was prepared from 3-(dimethylamino-methylene)-5-(2'-chloro-phenyl)-7-nitro-1,3-dihydro-2H-1,4-benzodiazepin-2-one and methyl iodide.

EXAMPLE 135

Using a procedure analogous to that described in Example 4, 1-(β-dimethylamino-ethyl)-3-(diethylamino-methylene)-5-(2'-chloro-phenyl)-7-nitro-1,3-dihydro-2H-1,4-benzodiazepin-2-one, m.p. 103°C, was prepared from 3-(diethylamino-methylene)-5-(2'-chloro-phenyl)-7-nitro-1,3-dihydro-2H-1,4-benzodiazepin-2-one and β-dimethylamino-ethyl chloride.

EXAMPLE 136

Using a procedure analogous to that described in Example 4, 1-(β-dimethylamino-ethyl)-3-(pyrrolidino-methylene)-5-(2'-chloro-phenyl)-7-nitro-1,3-dihydro-2H-1,4-benzodiazepin-2-one, m.p. 209°–210°C, was prepared from 3-(pyrrolidinomethylene)-5-(2'-chloro-phenyl)-7-nitro-1,3-dihydro-2H-1,4-benzodiazepin-2-one and β-dimethylamino-ethyl chloride.

EXAMPLE 137

Using a procedure analogous to that described in Example 4, 1-methyl-3-(piperidino-methylene)-5-(2'-chlorophenyl)-7-nitro-1,3-dihydro-2H-1,4-benzodiazepin-2-one, m.p. 139°–141°C, was prepared from 3-(piperidino-methylene)-5-(2'-chloro-phenyl)-7-nitro-1,3-dihydro-2H-1,4-benzodiazepin-2-one and methyl iodide.

EXAMPLE 138

Using a procedure analogous to that described in Example 4, 1-(β-dimethylamino-ethyl)-3-(piperidino-methylene)-5-(2'-chloro-phenyl)-7-nitro-1,3-dihydro-2H-1,4-benzodiazepin-2-one, m.p. 103°–106°C, was prepared from 3-(piperidinomethylene)-5-(2'-chloro-phenyl)-7-nitro-1,3-dihydro-2H-1,4-benzodiazepin-2-one and β-dimethylamino-ethyl chloride.

EXAMPLE 139

Using a procedure analogous to that described in Example 4, 1-methyl-3-(hexamethyleneimino-methylene)-5-(2'-chloro-phenyl)-7-nitro-1,3-dihydro-2H-1,4-benzodiazepin-2-one, m.p. 98°–105°C, was prepared from 3-(hexamethyleneimino-methylene)-5-(2'-chloro-phenyl)-7-nitro-1,3-dihydro-2H-1,4-benzodiazepin-2-one and methyl iodide.

EXAMPLE 140

Using a procedure analogous to that described in Example 4, 1-methyl-3-(morpholino-methylene)-5-(2'-chloro-phenyl)-7-nitro-1,3-dihydro-2H-1,4-benzodiazepin-2-one, m.p. 102°–105°C, was prepared from 3-(morpholino-methylene)-5-(2'-chloro-phenyl)-7-nitro-1,3-dihydro-2H-1,4-benzodiazepin-2-one and methyl iodide.

Example 141

7-Bromo-5-(2'-chloro-phenyl)-1,3-dihydro-3-(morpholino-methylene)-2H-1,4-benzodiazepin-2-one by method A A mixture consisting of 5 gm of 7-bromo-5-(2'-chloro-phenyl)-1,3-dihydro-2H-1,4-benzodiazepin-2-one and 17 ml of morpholino-diethoxy-methane was heated for 90 minutes at 140°C, while stirring, and the reaction mixture was then allowed to cool. The cool product was admixed with 150 ml of petroleum ether (b.p. 60°–80°C), the mixture was briefly brought to the boiling point, allowed to cool, and the crystalline substance which had separated out was collected by vacuum filtration and recrystallized from isopropanol, yielding the compound named in the heading, which decomposed slowly between 156° and 185°C.

EXAMPLE 142

Using a procedure analogous to that described in Example 141, 3-(dimethylamino-methylene)-5-(2'-chloro-phenyl)-7-fluoro-1,3-dihydro-2H-1,4-benzodiazepin-2-one, m.p. 210°–211°C, of the formula

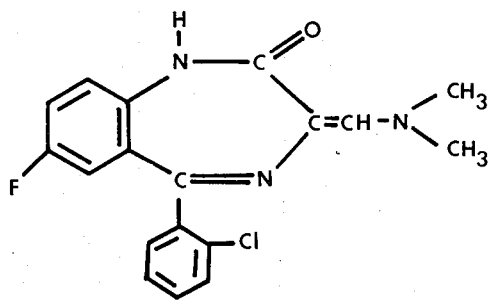

was prepared from 5-(2'-chloro-phenyl)-7-fluoro-1,3-dihydro-2H-1,4-benzodiazepin-2-one and N,N-dimethyl-formamide-diethylacetal.

EXAMPLE 143

Using a procedure analogous to that described in Example 141, 3-(morpholino-methylene)-5-(2'-chloro-phenyl)-7-fluoro-1,3-dihydro-2H-1,4-benzodiazepin-2-one, m.p. 243°–246°C (decomp.), was prepared from 5-(2'-chloro-phenyl)-7-fluoro-1,3-dihydro-2H-1,4-benzodiazepin-2-one and morpholino-diethoxy-methane.

EXAMPLE 144

Using a procedure analogous to that described in Example 141, 3-(dimethylamino-methylene)-5-(2'-chloro-phenyl)-7-iodo-1,3-dihydro-2H-1,4-benzodiazepin-2-one, m.p. 227°–230°C, of the formula

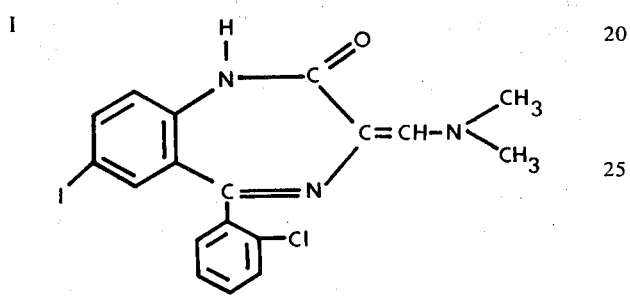

was prepared from 5-(2'-chloro-phenyl)-7-iodo-1,3-dihydro-2H-1,4-benzodiazepin-2-one and N,N-dimethyl-formamide-diethylacetal.

EXAMPLE 145

Using a procedure analogous to that described in Example 141, 3-(morpholino-methylene)-5-(2'-chloro-phenyl)-7-iodo-1,3-dihydro-2H-1,4-benzodiazepin-2-one, m.p. 218.5°–221°C, was prepared from 5-(2'-chloro-phenyl)-7-iodo-1,3-dihydro-2H-1,4-benzodiazepin-2-one and morpholino-diethoxy-methane.

EXAMPLE 146

5-(2'-Chloro-phenyl)-1,3-dihydro-3-(dimethylamino-methylene)-7-iodo-1-methyl-2H-1,4-benzodiazepin-2-one by method A A mixture consisting of 8 gm of 5-(2'-chloro-phenyl)-1,3-dihydro-7-iodo-1-methyl-2H-1,4-benzodiazepin-2-one and 16 ml of N,N-dimethyl-formamide-diethylacetal was heated for 90 minutes at 130°C. Thereafter, the reaction mixture was allowed to cool, and the crystalline substance which separated out was collected by vacuum filtration and washed with benzene and petroleum ether, yielding the compound named in the heading, which had a melting point of 182°–184°C.

EXAMPLE 147

Using a procedure analogous to that described in Example 146, 1-ethyl-3-(diethylamino-methylene)-5-(2'-chloro-phenyl)-7-chloro-1,3-dihydro-2H-1,4-benzodiazepin-2-one, an oily substance, of the formula

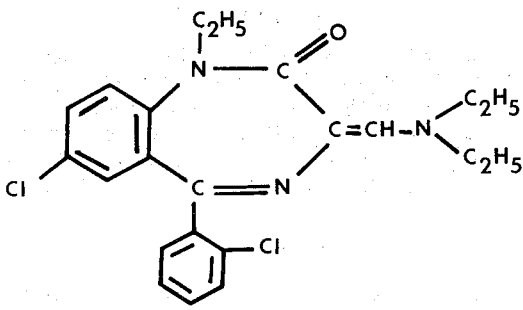

was prepared from 1-ethyl-5-(2'-chloro-phenyl)-7-chloro-1,3-dihydro-2H-1,4-benzodiazepin-2-one and N,N-diethyl-formamide-diethylacetal.

IR-spectrum in methylene chloride:

| | |
|---|---|
| 2940 cm$^{-1}$ | $CH_2$, $CH_3$ |
| 2570 cm$^{-1}$ | |
| 1635 cm$^{-1}$ | lactam C = O |
| 1575 cm$^{-1}$ | C = C, C = N |
| 1600 cm$^{-1}$ | |

EXAMPLE 148

Using a procedure analogous to that described in Example 146, 1-(2',2',2'-trifluoro-ethyl)-3-dimethylamino-methylene-5-(2''-chloro-phenyl)-7-bromo-1,3-dihydro-2H-1,4-benzodiazepin-2-one, m.p. 216°–217°C, of the formula

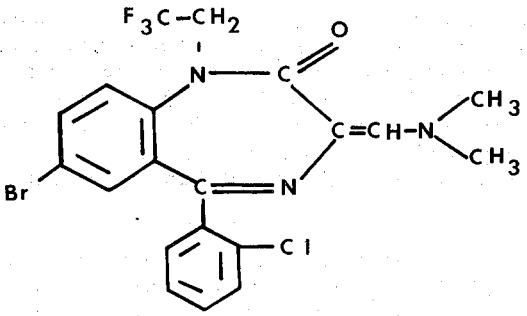

was prepared from 1-(2',2',2'-trifluoro-ethyl)-5-(2''-chloro-phenyl)-7-bromo-1,3-dihydro-2H-1,4-benzodiazepin-2-one and N,N-dimethyl-formamide-diethylacetal.

EXAMPLE 149

Using a procedure analogous to that described in Example 146, 1-methyl-3-(morpholino-methylene)-5-(2'-chloro-phenyl)-7-iodo-1,3-dihydro-2H-1,4-benzodiazepin-2-one, m.p. 193°–195°C, was prepared from 1-methyl-5-(2'-chloro-phenyl)-7-iodo-1,3-dihydro-2H-1,4-benzodiazepin-2-one and morpholino-diethoxy-methane.

EXAMPLE 150

3-(Amino-methylene)-7-chloro-5-(2'-fluoro-phenyl)-1,3-dihydro-2H-1,4-benzodiazepin-2-one by method B Dry, gaseous ammonia was passed for four hours into a solution of 9 gm of 7-chloro-1,3-dihydro-3 -dimethylamino-methylene)-5-(2'-fluoro-phenyl)-2H-1,4-benzodiazepin-2-one and a spatulatipful of ammonium chloride in 70 ml of dimethylformamide at 80°C, accompanied by stirring. Thereafter, the reaction solution was evaporated to dryness in vacuo, and the yellowish-brown residue was crystallized from isopropanol/petroleum ether, yielding the compound named in the heading, which had a melting point of 275°–280°C.

EXAMPLE 151

7-Chloro-5-(2'-chloro-phenyl)-1,3-dihydro-1-methyl-3-(thiomorpholino-methylene)-2H-1,4-benzodiazepin-2-one-S-oxide by method B 5.4 gm of thiomorpholine-S-oxide were added to a solution of 11.2 gm of 7-chloro-5-(20'-chloro-phenyl)-1,3-dihydro-3-(dimethylamino-methylene)-1-methyl-2H-1,4-benzodiazepin-2-one in 70 ml of dimethylformamide, and the mixture was heated at 140°C for 24 hours. Thereafter, the reaction solution was evaporated to dryness in vacuo, and the yellowish-brown residue was crystallized from isopropanol, yielding the compound of the formula

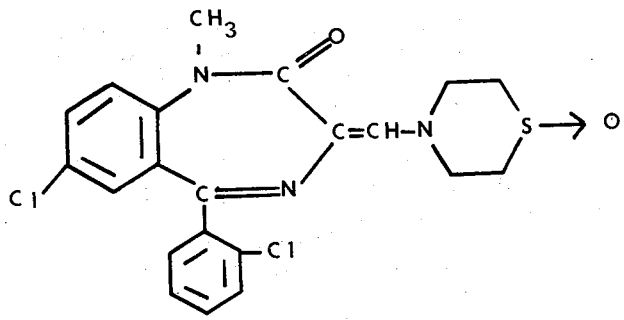

which had a melting point of 185°–191°C (decomp.).

EXAMPLE 152

Using a procedure analogous to that described in Example 150, 3-(amino-methylene)-5-(2'-chlorophenyl)-7-fluoro-1,3-dihydro-2H-1,4-benzodiazepin-2-one, m.p. 173°–174°C, was prepared from 3-(dimethylamino-methylene)-5-(2'-chloro-phenyl)-7-fluoro-1,3-dihydro-2H-1,4-benzodiazepin-2-one and ammonia.

EXAMPLE 153

Using a procedure analogous to that described in Example 150, 1-methyl-3-(amino-methylene)-5-(2'-chloro-phenyl)-7-fluoro-1,3-dihydro-2H-1,4-benzodiazepin-2-one, m.p. 105°–110°C, was prepared from 1-methyl-3-(dimethylamino-methylene)-5-(2'-chloro-phenyl)-7-fluoro-1,3-dihydro-2H-1,4-benzodiazepin-2-one and ammonia.

EXAMPLE 154

Using a procedure analogous to that described in Example 150, 3-(ethylamino-methylene)-5-(2'-chloro-phenyl)-7-fluoro-1,3-dihydro-2H-1,4-benzodiazepin-2-one, m.p. 138°–141°C, was prepared from 3-(dimethylamino-methylene)-5-(2'-chloro-phenyl)-7-fluoro-1,3-dihydro-2H-1,4-benzodiazepin-2-one and ethylamine.

EXAMPLE 155

Using a procedure analogous to that described in Example 150, 3-(ethylamino-methylene)-5-(2'-chloro-phenyl)-7-fluoro-1,3-dihydro-2H-1,4-benzodiazepin-2-one, m.p. 138°–141°C, was prepared from 3-(dimethylamino-methylene)-5-(2'-chloro-phenyl)-7-fluoro-1,3-dihydro-2H-1,4-benzodiazepin-2-one and ethylamine.

EXAMPLE 156

Using a procedure analogous to that described in Example 150, 1-methyl-3-(methylamino-methylene)-5-phenyl-7-chloro-1,3-dihydro-2H-1,4-benzodiazepin-2-one, m.p. 201°–202°C, was prepared from 1-methyl-3-(dimethylamino-methylene)-5-phenyl-7-chloro-1,3-dihydro-2H-1,4-benzodiazepin-2-one and methylamine.

EXAMPLE 157

Using a procedure analogous to that described in Example 150, 1-methyl-3-(methylamino-methylene)-5-(2'-chloro-phenyl)-7-chloro-1,3-dihydro-2H-1,4-benzodiazepin-2-one, m.p. 155°–158°C, was prepared from 1-methyl-3-(dimethylamino-methylene)-5-(2'-chloro-phenyl)-7-chloro-1,3-dihydro-2H-1,4-benzodiazepin-2-one and methylamine.

EXAMPLE 158

Using a procedure analogous to that described in Example 141, 1-methyl-3-(thiomorpholine-methylene)-5-(2'-chloro-phenyl)-7-chloro-1,3-dihydro-2H-1,4-benzodiazepin-2-one, a foamy solid, was prepared from 1-methyl-5-(2'-chloro-phenyl)-7-chloro-1,3-dihydro-2H-1,4-benzodiazepin-2-one and thiomorpholino-diethoxy-methane.

IR-spectrum in methylene chloride:

| | |
|---|---|
| 2800 cm$^{-1}$ | N-alkyl |
| 1650 cm$^{-1}$ | lactam-CO |
| 1600 cm$^{-1}$ | C = C |
| 1575 cm$^{-1}$ | C = N |
| 1500 cm$^{-1}$ | |

EXAMPLE 159

Using a procedure analogous to that described in Example 150, 3-(amino-methylene)-5-(2'-chloro-phenyl)-7-bromo-1,3-dihydro-2H-1,4-benzodiazepin-2-one, m.p. 216°–218°C (decomp.), was prepared from 3-(dimethylamino-methylene)-5-(2'-chloro-phenyl)-7-bromo-1,3-dihydro-2H-1,4-benzodiazepin-2-one and ammonia.

EXAMPLE 160

Using a procedure analogous to that described in Example 150, 1-methyl-3-(methylamino-methylene)-5-(2'-chloro-phenyl)-7-bromo-1,3-dihydro-2H-1,4- benzodiazepin-2-one, m.p. 157°–158°C, was prepared from 1-methyl-3-(dimethylamino-methylene)-5-(2'-chloro-phenyl)-7-bromo-1,3-dihydro-2H-1,4-benzodiazepin-2-one and methylamine.

EXAMPLE 161

Using a procedure analogous to that described in Example 150, 3-(ethylamino-methylene)-5-(2'-chloro-phenyl)-7-bromo-1,3-dihydro-2H-1,4-benzodiazepin-2-one, m.p. 227°–229°C, was prepared from 3-(dimethylamino-methylene)-5-(2'-chloro-phenyl)-7-bromo-1,3-dihydro-2H-1,4-benzodiazepin-2-one and ethylamine.

EXAMPLE 162

Using a procedure analogous to that described in Example 150, 3-(amino-methylene)-5-(2'-chloro-phenyl)-7-iodo-1,3-dihydro-2H-1,4-benzodiazepin-2-one, m.p. 167°–172°C (decomp.), was prepared from 3-(dimethylamino-methylene)-5-(2'-chloro-phenyl)-7-iodo-1,3-dihydro-2H-1,4-benzodiazepin-2-one and ammonia.

EXAMPLE 163

Using a procedure analogous to that described in Example 150, 1-methyl-3-(amino-methylene)-5-(2'-chloro-phenyl)-7-iodo-1,3-dihydro-2H-1,4-benzodiazepin-2-one, m.p. 130°C (decomp.), was prepared from 1-methyl-3-(dimethylamino-methylene)-5-(2'-chloro-phenyl)-7-iodo-1,3-dihydro-2H-1,4-benzodiazepin-2-one and ammonia.

EXAMPLE 164

Using a procedure analogous to that described in Example 150, 3-(ethylamino-methylene)-5-(2'-chloro-phenyl)-7-iodo-1,3-dihydro-2H-1,4-benzodiazepin-2-one, m.p. 212°–214°C, was prepared from 3-(dimethylamino-methylene)-5-(2'-chloro-phenyl)-7-iodo-1,3-dihydro-2H-1,4-benzodiazepin-2-one and ethylamine.

EXAMPLE 165

Using a procedure analogous to that described in Example 150, 1-methyl-3-(ethylamino-methylene)-5-(2'-chloro-phenyl)-7-iodo-1,3-dihydro-2H-1,4-benzodiazepin-2-one, m.p. 202°–206°C, was prepared from 1-methyl-3-(dimethlamino-methylene)-5-(2'-chloro-phenyl)-7-iodo-1,3-dihydro-2H-1,4-benzodiazepin-2-one and ethylamine.

EXAMPLE 166

Using a procedure analogous to that described in Example 150, 1-methyl-3-(amino-methylene)-5-(2'-chloro-phenyl)-7-nitro-1,3-dihydro-2H-1,4-benzodiazepin-2-one, m.p. 140°–143°C (decomp.), was prepared from 1-methyl-3-(dimethylamino-methylene)-5-(2'-chloro-phenyl)-7-nitro-1,3-dihydro-2H-1,4-benzodiazepin-2-one and ammonia.

EXAMPLE 167

5-(2'-Chloro-phenyl)-1,3-dihydro-7-fluoro-1-methyl-3-(morpholino-methylene)-2H-1,4-benzodiazepin-2-one by method C 1.6 gm of a methanolic 30% sodium methylate solution were added to a suspension of 2 gm of 5-(2'-chloro-phenyl)-1,3-dihydro-7-fluoro-3-(morpholino-methylene)-2H-1,4-benzodiazepin-2-one in 50 ml of dimethylformamide at room temperature, whereby a reddish-brown solution was immediately formed. The resulting solution was cooled to 0°C, and then 2.1 gm of methyl iodide were added dropwise thereto. After one hour the mixture was poured into ice water, and the precipitate formed thereby was collected by vacuum filtration and dried over phosphorus pentoxide, yielding the compound named in the heading, which had a melting point of 110°–115°C.

EXAMPLE 168

Using a procedure analogous to that described in Example 167, 1-methyl-3-(dimethylamino-methylene)-5-(2'-chloro-phenyl)-7-fluoro-1,3-dihydro-2H-1,4-benzodiazepin-2-one, m.p. 177°–179°C, was prepared from 3-(dimethylamino-methylene)-5-(2'-chloro-phenyl)-7-fluoro-1,3-dihydro-2H-1,4-benzodiazepin-2-one, sodium methylate and methyl iodide.

The compounds embraced by formula I above have useful pharmacodynamic properties. More particularly, they exhibit sedative, tranquilizing, muscle-relaxing and anticonvulsive activities in warm-blooded animals, such as mice.

The muscle-relaxing, sedative and anticonvulsive activities of the compound of the formula I were ascertained by standard pharmacological test methods. The results of these tests for certain selected compounds, which are representative and illustrative of the genus, are shown below, where A = 7-Chloro-5-(2'-chloro-phenyl)-1,3-dihydro-1-methyl-3-(morpholino-methylene)-2H-1,4-benzodiazepin-2-one, B = 3-(Amino-methylene)-7-chloro-5-(2'-chloro-phenyl)-1,3-dihydro-2H-1,4-benzodiazepin-2-one, C = 3-(Ethylamino-methylene)-7-chloro-5-(2'-chloro-phenyl)-1,3-dihydro-1-methyl-2H-1,4-benzodiazepin-2-one, D = 7-Bromo-5-(2'-chloro-phenyl)-1,3-dihydro-1-methyl-3-(morpholino-methylene)-2H-1,4-benzodiazepin-2-one, E = 3-(Amino-methylene)-7-bromo-5-(2'-chloro-phenyl)-1,3-dihydro-1-methyl-2H-1,4-benzodiazepin-2-one, F = 3-(Amino-methylene)-7-bromo-5-(2'-chloro-phenyl)-1,3-dihydro-2H-1,4-benzodiazepin-2-one, G = 3-(Ethylamino-methylene)-7-bromo-5-(2'-chloro-phenyl)-1,3-dihydro-2H-1,4-benzodiazepin-2-one, and H = 3-(Amino-methylene)-5-(2'-chloro-phenyl)-1,3-dihydro-7-iodo-1-methyl-2H-1,4-benzodiazepin-2-one.

1. Muscle-relaxing and sedative activity

The muscle-relaxing and sedative activities were tested by the method of Young and Lewis [Science 105, 368 (1947)]on female NMRI-mice of our own breed with a body weight between 20 and 26 gm by means of slowly turning wire-mesh cylinders, inclined at 30° from the vertical (length : 43 cm; diameter : 22 cm; mesh-size of the wire netting : 0.6 cm). After peroral administration of the test compound in the form of a 1% suspension in tylose to groups of 10 mice/dose their holding ability in the slowly rotating cylinders was tested (2 rotations/minute) against a control group. The median effective dose ($ED_{50}$) was graphically determined which caused 50% of the animals to fall out of the cylinders at various time intervals after administration.

TABLE I

| Compound | ED$_{50}$ mgm/kg p.o. | | | |
|---|---|---|---|---|
| | after 30–60 min. | after 90–120 min. | after 210–240 min. | after 270–300 min. |
| A | 14 | 5 | 14 | 3 |
| B | 13 | 3 | 10 | 11 |
| C | 2 | 3 | 11 | 3 |
| D | 33 | 26 | 16 | 13 |
| E | 7 | 7 | 5 | 6 |
| F | 0.5 | 0.7 | 0.7 | 1.9 |
| G | 2.4 | 1.25 | 2.1 | 2.4 |
| H | 2.6 | 1.5 | 2.7 | 1.6 |

2. Anticonvulsive activity

The anticonvulsive activity was tested in terms of the protective effect against the maximum electro-shock-spasm in male NMRI-mice of our own breed with a body weight between 20 and 26 gm analogous to Swinyard, Brown and Goodman [J. Pharmacol. exp. Therap. 106, 319 (1952)]. The animals were exposed to an alternating current of 50 cycles and 50 milliamperes (duration of stimulation 0.2 seconds), where the occurrence of the tonic extensor spasm was valued as positive. After peroral administration of the test compound in the form of a 1% suspension in tylose, the dose (ED$_{50}$) was graphically determined which protected 50% of the animals against the tonic extensor component of the back extremities after various time intervals.

TABLE II

| Compound | ED$_{50}$ mgm/kg p.o. | | |
|---|---|---|---|
| | after 30 min. | after 150 min. | after 300 min. |
| A | 100 | 18 | 13 |
| B | 85 | 28 | 43 |
| C | 200 | 28 | 36 |
| D | 200 | 31 | 34 |
| E | 18 | 17 | 26 |
| F | 70 | 14.5 | 16 |
| G | 37 | 8.8 | 22 |
| H | 38 | 30 | 16 |

3. Effect on spontaneous motility

The sedative activity was further determined on mice in terms of the decreasing effect upon the spontaneous motility. The motility of 8 mice per dose of test compound was compared to the motility of 8 control animals; each group was placed into separate motility-measuring cages (diameter : 25 cm), with 10 photoelectric cells in the floor and a light source above the cage. After peroral administration of the test compound the dose was graphically determined which decreased the motility by 50%, compared to the control animals, at various time intervals after administration.

TABLE III

| Compound | ED$_{50}$ mgm/kg p.o. | |
|---|---|---|
| | after 90–95 min. | after 150–155 min. |
| D | 4.4 | 5.2 |
| F | 8.15 | 3.76 |
| G | 1.56 | 2.45 |

It should be added that the compounds of the formula I are virtually non-toxic. For instance, by standard acute toxicity tests were determined that even massive doses of 6400 mgm/kg p.o. of compound A or 3200 mgm/kg p.o. of compounds B or C produced no deaths in a group of 10 adult laboratory mice within 14 days.

For pharmaceutical purposes the compounds of the formula I are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, suppositories and the like. One effective dosage unit of the compounds according to the present invention is from 0.033 to 0.34 mgm/kg body weight, preferably 0.083 to 0.167 mgm/kg body weight; the daily dose rate is 0.083 to 1.34 mgm/kg body weight, preferably 0.16 to 0.67 mgm/kg body weight.

The following examples illustrate a few pharmaceutical dosage unit compositions comprising a compound of the formula I as an active ingredient and represent the best modes contemplated of putting the invention into practical use. The parts are parts by weight unless otherwise specified.

EXAMPLE 169

Tablets

The tablet composition is compounded from the following ingredients:

| | |
|---|---|
| 3-(Ethylamino-methylene)-7-bromo-5-(2'-chloro-phenyl)-1,3-dihydro-2H-1,4-benzodiazepin-2-one | 5 parts |
| Lactose | 75 parts |
| Corn starch | 37 parts |
| Gelatin | 2 parts |
| Magnesium stearate | 1 parts |
| Total | 120 parts |

Preparation:

The benzodiazepinone compound, the lactose and the corn starch are intimately admixed with each other, the mixture is granulated through a 1.5 mm-mesh screen with an aqueous 8% solution of the gelatin; the granulate is dried at 45°C and again passed through a 1.0 mm-mesh screen, and the dry granulate thus obtained is admixed with the magnesium stearate. The resulting composition is compressed into 120 mgm-tablets in a conventional tablet making machine. Each tablet contains 5 mgm of the benzodiazepinone compound and is an oral dosage unit composition with effective sedative, tranquilizing, muscle-relaxing and anticonvulsive action.

EXAMPLE 170

Coated tablets

The tablets prepared pursuant to Example 169 are coated with a thin shell consisting essentially of a mixture of sugar and talcum, and the coated tablets are polished with beeswax. The coated tablets contain the same amount of active ingredient and have the same pharmacological effect as the uncoated tablets of Example 169.

EXAMPLE 171

Suppositories

The suppository composition is compounded from the following ingredients:

| | |
|---|---:|
| 3-(Ethylamino-methylene)-7-bromo-5-(2'-chloro-phenyl)-1,3-dihydro-2H-1,4-benzodiazepin-2-one | 30 parts |
| Suppository base (e.g. cocoa butter) | 1670 parts |
| Total | 1700 parts |

Preparation:

The milled benzodiazepinone compound is blended with the aid of an immersion homogenizer into the suppository base which had previously been melted and cooled to 40°C. 1700 mgm-portions of the mixture are poured into cooled suppository molds and allowed to harden therein. Each suppository contains 30 mgm of the benzodiazepinone compound and is a rectal dosage unit composition with effective sedative, tranquilizing, muscle-relaxing and anticonvulsive action.

EXAMPLE 172

Gelatin capsules

The capsule filler composition is compounded from the following ingredients:

| | |
|---|---:|
| 3-(Ethylamino-methylene)-7-chloro-5-(2'-chloro-phenyl)-1,3-dihydro-1-methyl-2H-1,4-benzodiazepin-2-one | 5 parts |
| Corn starch, dry | 174 parts |
| Magnesium stearate | 1 parts |
| Total | 180 parts |

Preparation:

The ingredients are intimately admixed with each other, and 180 mgm-portions of the mixture are filled into size 4 gelatin capsules. Each capsule contains 5 mgm of the benzodiazepinone compound and is an oral dosage unit composition with effective sedative, tranquilizing, muscle-relaxing and anticonvulsive action.

Analogous results were obtained when any one of the other benzodiazepinones embraced by formula I was substituted for the particular benzodiazepinone in Examples 170 through 172. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A pharmaceutical dosage unit composition consisting essentially of an inert pharmaceutical carrier and an effective sedative, tranquilizing, muscle-relaxing or anticonvulsive amount of a compound of the formula

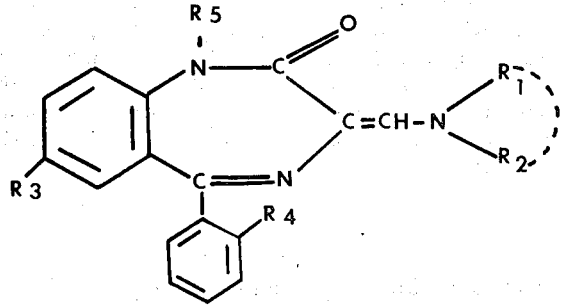

wherein $R_1$ and $R_2$ are each hydrogen, cycloalkyl of 3 to 6 carbon atoms, phenyl, $$-A-Y$$

where
A is alkyl of 1 to 5 carbon atoms or alkenyl of 1 to 5 carbon atoms, and
Y is furyl, di(lower alkyl)amino, hydroxyl, lower alkoxy-carbonyl or carbamido,
or, together with each other and the nitrogen atom to which they are attached, pyrrolidino, piperidino, hexamethyleneimino, morpholino, thiomorpholino, thiomorpholino-S-oxide or N'-lower alkyl-piperazino,
$R_3$ is halogen, nitro or trifluoromethyl,
$R_4$ is hydrogen, halogen or trifluoromethyl, and
$R_5$ is hydrogen, lower alkyl, (cycloalkyl of 3 to 6 carbon atoms)-methyl, lower alkyl-amino-lower alkyl, di(lower alkyl)amino-lower alkyl or trifluoromethyl-lower alkyl.

2. A composition of claim 1, wherein said compound is of the said formula
wherein
$R_1$ and $R_2$ are each hydrogen or alkyl of 1 to 3 carbon atoms or, together with each other and the nitrogen atom to which they are attached, morpholino or thiomorpholino-S-oxide,
$R_3$ and $R_4$ are each halogen, and
$R_5$ is hydrogen or alkyl of 1 to 3 carbon atoms.

3. A composition of claim 1, wherein said compound is 3-(amino-methylene)-7-bromo-5-(2'-chloro-phenyl)-1,3-dihydro-1-methyl-2H-1,4-benzodiazepin-2-one.

4. A composition of claim 1, wherein said compound is 3-(ethyl-amino-methylene)-7-chloro-5-(2'-chloro-phenyl)-1,3-dihydro-1-methyl-2H-1,4-benzodiazepin-2-one.

5. A composition of claim 1, wherein said compound is 3-(amino-methylene)-7-chloro-5-(2'-chloro-phenyl)-1,3-dihydro-2H-1,4-benzodiazepin-2-one.

6. A composition of claim 1, wherein said compound is 7-bromo-5-(2'-chloro-phenyl)-1,3-dihydro-1-methyl-3-morpholino-methylene)-2H-1,4-benzodiazepin-2-one.

7. A composition of claim 1, wherein said compound is 7-chloro-5-(2'-chloro-phenyl)-1,3-dihydro-1-methyl-3-(morpholino-methylene)-2H-1,4-benzodiazepin-2-one.

8. A composition of claim 1, wherein said compound is 3-(amino-methylene)-7-bromo-5-(2'-chloro-phenyl)-1,3-dihydro-2H-1,4-benzodiazepin-2-one.

9. A composition of claim 1, wherein said compound is 3-(ethylamino-methylene)-7-bromo-5-(2'-chloro-phenyl)-1,3-dihydro-2H-1,4-benzodiazepin-2-one.

10. A composition of claim 1, wherein said compound is 3-(amino-methylene)-5-(2'-chloro-phenyl)-1,3-dihydro-7-iodo-1-methyl-2H-1,4-benzodiazepin-2-one.

11. The method of inducing sedation, relaxing the muscles, suppressing convulsions, or quieting or calming anxiety or tension in a warm-blooded animal in need of such treatment, which comprises perorally, parenterally or rectally administering to said animal an effective sedative, muscle-relaxing, anticonvulsive or tranquilizing amount of a compound of the formula

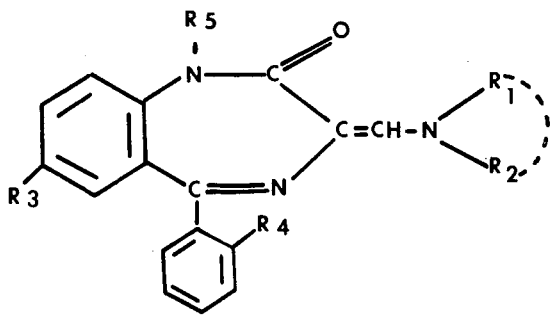

wherein
R₁ and R₂ are each hydrogen, cycloalkyl of 3 to 6 carbon atoms, phenyl,

—A—Y where
A is alkyl of 1 to 5 carbon atoms or alkenyl of 1 to 5 carbon atoms, and
Y is furyl, di(lower alkyl)amino, hydroxyl, lower alkoxy-carbonyl or carbamido, or, together with each other and the nitrogen atom to which they are attached, pyrrolidino, piperidino, hexamethyleneimino, morpholino, thiomorpholino, thiomorpholino-S-oxide or N'-lower alkyl-piperazino,
R₃ is halogen, nitro or trifluoromethyl,
R₄ is hydrogen, halogen or trifluoromethyl, and
R₅ is hydrogen, lower alkyl, (cycloalkyl of 3 to 6 carbon atoms)-methyl, lower alkyl-amino-lower alkyl, di(lower alkyl)amino-lower alkyl or trifluoromethyl-lower alkyl.

12. The method of claim 11, where said compound is of the said formula wherein
R₁ and R₂ are each hydrogen or alkyl of 1 to 3 carbon atoms or, together with each other and the nitrogen atom to which they are attached, morpholino or thiomorpholino-S-oxide,
R₃ and R₄ are each halogen, and
R₅ is hydrogen or alkyl of 1 to 3 carbon atoms.

13. The method of claim 11, wherein said compound is 3-(amino-methylene)-7-bromo-5-(2'-chlorophenyl)-1,3-dihydro-1-methyl-2H-1,4-benzodiazepin-2-one.

14. The method of claim 11, wherein said compound is 3-(ethyl-amino-methylene)-7-chloro-5-(2'-chlorophenyl)-1,3-dihydro-1-methyl-2H-1,4-benzodiazepin-2-one.

15. The method of claim 11, wherein said compound is 3-(amino-methylene)-7-chloro-5-(2'-chlorophenyl)-1,3-dihydro-2H-1,4-benzodiazepin-2-one.

16. The method of claim 11, wherein said compound is 7-bromo-5-(2'-chloro-phenyl)-1,3-dihydro-1-methyl-3-(morpholino-methylene)-2H-1,4-benzodiazepin-2-one.

17. The method of claim 11, wherein said compound is 7-chloro-5-(2'-chloro-phenyl)-1,3-dihydro-1-methyl-3-(morpholino-methylene)-2H-1,4-benzodiazepin-2-one.

18. The method of claim 11, wherein said compound is 3-(amino-methylene)-7-bromo-5-(2'-chlorophenyl)-1,3-dihydro-2H-1,4-benzodiazepin-2-one.

19. The method of claim 11, wherein said compound is 3-(ethylamino-methylene)-7-bromo-5-(2'-chlorophenyl)-1,3-dihydro-2H-1,4-benzodiazepin-2-one.

20. The method of claim 11, wherein said compound is 3-(amino-methylene)-5-(2'-chloro-phenyl)-1,3-dihydro-7-iodo-1-methyl-2H-1,4-benzodiazepin-2-one.

* * * * *

UNITED STATES PATENT OFFICE
CERTIFICATE OF CORRECTION

Patent No. 3,956,492  Dated May 11, 1976

Inventor(s) HELMUT PIEPER, GERD KRÜGER, JOHANNES KECK, KLAUS-REINHOLD NOLL, JOACHIM KAHLING It is certified that error appears in the above-identified patent and that said Letters Patent are hereby corrected as shown below:

| | |
|---|---|
| In Col. 3, Line 64 | "example" should read -- examples -- |
| In Col. 7, Line 17 | "-110°C" should read -- -101°C -- |
| In Col. 15, Line 66 | after "1," -- 4 -- should be deleted. |
| In Col. 21, Line 30 | "2one" should read -- 2-one -- |
| In Col. 21, Line 68 | "-diethy(amino-" should read -- -diethylamino- -- |
| In Col. 23, Line 63 | "tert," should read -- tert. -- |
| In Col. 24, Line 20 | "(dimethyaminomethylene)" should read -- (dimethylaminomethylene) -- |
| In Col. 25, Line 17 | After "Using" insert -- a -- |
| In Col. 32, Line 21 | Insert -- 2960cm$^{-1}$ -- before "2940cm$^{-1}$" |
| In Col. 33, Line 23 | "20'" should read -- 2' -- |

Signed and Sealed this

Thirty-first Day of August 1976

[SEAL]

Attest:

RUTH C. MASON
Attesting Officer

C. MARSHALL DANN
Commissioner of Patents and Trademarks